（12) United States Patent
Kuwahara

(10) Patent No.: US 10,597,719 B2
(45) Date of Patent: Mar. 24, 2020

(54) DETECTION KIT AND SIMPLE METHOD FOR DETECTING TARGET NUCLEIC ACIDS

(71) Applicant: National University Corporation Gunma University, Gunma (JP)

(72) Inventor: Masayasu Kuwahara, Gunma (JP)

(73) Assignee: National University Corporation Gunma University, Gunma (JP)

( * ) Notice: Subject to any disclaimer, the term of this patent is extended or adjusted under 35 U.S.C. 154(b) by 188 days.

(21) Appl. No.: 15/560,837

(22) PCT Filed: Mar. 23, 2016

(86) PCT No.: PCT/JP2016/059262
§ 371 (c)(1),
(2) Date: Sep. 22, 2017

(87) PCT Pub. No.: WO2016/152936
PCT Pub. Date: Sep. 29, 2016

(65) Prior Publication Data
US 2019/0040465 A1    Feb. 7, 2019

(30) Foreign Application Priority Data

Mar. 24, 2015  (JP) ................. 2015-061654

(51) Int. Cl.
*C12Q 1/68* (2018.01)
*C12Q 1/6876* (2018.01)
*C12Q 1/6844* (2018.01)

(52) U.S. Cl.
CPC ......... *C12Q 1/6876* (2013.01); *C12Q 1/6844* (2013.01)

(58) Field of Classification Search
CPC ............ C12Q 1/6876; C12Q 2525/161; C12Q 2525/307; C12Q 2531/125; C12Q 2565/133
See application file for complete search history.

(56) References Cited

FOREIGN PATENT DOCUMENTS

| JP | 5-146299 | 6/1993 |
| JP | 2012-080871 | 4/2012 |
| WO | WO-2011/051709 A1 | 5/2011 |
| WO | WO-2015-019194 A2 | 2/2015 |

OTHER PUBLICATIONS

Kabori et al., "Expanding Possibilities of Rolling Circle Amplification as a Biosensing Platform", Anal. Sci., vol. 30, No. 1, 2014, pp. 59-64.
Lin et al., "A Portable Microchip for Ultrasensitive and High-Throughput Assay of Thrombin by Rolling Circle Amplification and hemin/G-quadruplex System", Biosens. Bioelectron., vol. 56, 2014, pp. 71-76.
Kataoka et al., "Minimal Thioflavin T Modifications Improve Visual Discrimination of Quanine-quadruplex Topologies and Alter Compound-induced Topological Structures", Anal. Chem., vol. 86, Issue 24, 2014, pp. 12078-12084.
Search Report in International Application No. PCT/JP2016/059262 dated Jun. 21, 2016, 2 pages.
Kataoka et al., "Minimal Thioflavin T Modifications Improve Visual Discrimination of Guanine-quadruplex Topologies and Alter Compound-induced Topological Structures", Anal. Chem., vol. 86, Issue 24, 2014, pp. 12078-12084.
International Preliminary Report on Patentability in International Application No. PCT/JP2016/059262 dated Oct. 5, 2017, 8 pages.

*Primary Examiner* — David C Thomas
(74) *Attorney, Agent, or Firm* — Marshall, Gerstein & Borun LLP

(57) ABSTRACT

An RNA detection kit comprising: (i) a single-stranded circular DNA template containing: a sequence of 10 to 30 bases complementary to a first portion of a target RNA; a primer-binding sequence of 7 to 8 bases adjacent to 5'-side thereof; and a sequence complementary to a detection reagent-binding sequence such as a guanine quadruplex-forming sequence; (ii) an oligonucleotide primer containing: a sequence of 8 to 15 bases complementary to a second portion adjacent to the 3'-side of the first portion of the target RNA; and a sequence of 7 to 8 bases adjacent to 3'-side thereof and complementary to the primer-binding sequence of the single-stranded circular DNA template; and (iii) a detection reagent such as a guanine quadruplex-binding reagent; is provided.

18 Claims, 11 Drawing Sheets

Specification includes a Sequence Listing.

Immobilization of Primer A (18mer) on beads

Samples

①: Negative control

②: Reaction

Immobilization of Primer B (19mer) on beads

③: Negative control

④: Reaction

| | Template | | Primer | | | | Target RNA |
|---|---|---|---|---|---|---|---|
| | Circular_Cid_Pre_T | Circular_Cid_Mai_T | Cid_Pre_PP | Cid_P18 | Cid_Mai_PP | Cid_Mai_P18 | Cid_40 |
| 1 | - | + | - | - | - | - | - |
| 2 | - | + | - | - | - | + | - |
| 3 | - | + | - | + | - | - | - |
| 4 | - | + | - | - | - | - | + |
| 5 | + | + | + | - | - | - | - |
| 6 | + | + | - | + | - | - | + |
| 7 | - | + | - | - | + | - | - |
| 8 | + | + | + | - | - | + | - |
| 9 | + | + | - | + | - | + | + |

DETECTION KIT AND SIMPLE METHOD FOR DETECTING TARGET NUCLEIC ACIDS

TECHNICAL FIELD

The present invention relates to reagents for simply and efficiently detecting a target RNA, and a detection method using the reagents.

BACKGROUND ART

In recent years, development of methods targeting RNA molecules such as mRNAs and miRNAs for detection of diseases and stresses is attracting attention. As methods for quantification and detection of RNA, methods using real-time PCR are known. However, their use for simple tests at clinics or for self-medication is difficult since they require expensive devices and high usage cost, as well as complicated operation.

On the other hand, a method in which RNA is detected by a rolling circle amplification method has been disclosed in Patent Document 1. However, this method enables only detection of a sequence at the 3'-end since the method uses analyte RNA as a primer. This method is also insufficient from the viewpoint of the amplification efficiency and the detection efficiency.

PRIOR ART DOCUMENT

Patent Document

[Patent Document 1] JP 2012-080871 A

SUMMARY OF THE INVENTION

Problems to be Solved by the Invention

An object of the present invention is to provide a kit and a method for efficiently detecting a target RNA by a simple method.

Means for Solving the Problems

In order to solve the above problems, the present inventors intensively studied. As a result, the present inventors discovered that simple and efficient detection of a target RNA is possible by hybridizing the target RNA with a single-stranded circular DNA and a primer to form a complex of these three molecules, performing amplification from the primer by a rolling circle amplification (RCA) method, and then detecting a detection reagent-binding sequence (for example, guanine quadruplex-containing sequence) contained in the amplification product using a detection reagent such as a thioflavin T (ThT) derivative, thereby completing the present invention.

That is, according to the first embodiment of the present invention, an RNA detection kit comprising:
  (i) a single-stranded circular DNA template containing:
    a sequence of 10 to 30 bases complementary to a first portion of a target RNA;
    a primer-binding sequence of 7 to 8 bases adjacent to 5'-side thereof; and
    a sequence complementary to a detection reagent-binding sequence such as a guanine quadruplex-forming sequence;
  (ii) an oligonucleotide primer containing:
    a sequence of 8 to 15 bases complementary to a second portion adjacent to the 3'-side of the first portion of the target RNA; and
    a sequence of 7 to 8 bases adjacent to 3'-side thereof and complementary to the primer-binding sequence of the single-stranded circular DNA template; and
  (iii) a detection reagent such as a guanine quadruplex-binding reagent; is provided.

According to the second embodiment of the present invention, an RNA detection kit comprising:
  (i) a first single-stranded circular DNA template containing:
    a sequence of 10 to 30 bases complementary to a first portion of a target RNA;
    a first primer-binding sequence of 7 to 8 bases adjacent to 5'-side thereof; and
    a second single-stranded circular DNA-binding sequence;
  (ii) a first oligonucleotide primer containing:
    a sequence of 8 to 15 bases complementary to a second portion adjacent to the 3'-side of the first portion of the target RNA; and
    a sequence of 7 to 8 bases adjacent to 3'-side thereof and complementary to the first primer-binding portion of the first single-stranded circular DNA template;
  (iii) a second single-stranded circular DNA containing:
    the same sequence as the second single-stranded circular DNA-binding sequence of the first single-stranded circular DNA;
    a second primer-binding sequence adjacent to 3'-side thereof; and
    a sequence complementary to a detection reagent-binding sequence such as a guanine quadruplex-forming sequence;
  (iv) a second oligonucleotide primer containing:
    the same sequence as the portion adjacent to the 5'-side of the second single-stranded circular DNA-binding sequence of the first single-stranded circular DNA; and
    a sequence adjacent to 3'-side thereof and complementary to the second primer-binding sequence of the second single-stranded circular DNA; and
  (v) a detection reagent such as a guanine quadruplex-binding reagent; is provided.

According to the present invention, a method for detecting a target RNA using the above kit, the method comprising the steps of:
  hybridizing the single-stranded circular DNA template and the primer with the target RNA;
  performing nucleic acid amplification reaction based on the target RNA by rolling circle amplification; and
  detecting an amplified detection reagent-binding sequence such as a guanine quadruplex-containing sequence with a detection reagent such as a guanine quadruplex-binding reagent;
is also provided.

Effect of the Invention

According to the present invention, in the presence of a target RNA sequence, a single-stranded circular DNA and a primer hybridize with the target RNA sequence, and, from the resulting hybridization product, a DNA chain containing a number of detection reagent-binding sequences such as guanine quadruplex-containing sequences linearly bound to each other is produced. By staining the DNA chain with a detection reagent such as ThT (derivative), the RNA sequence can be specifically detected. Since the present invention uses the RCA method, in which the reaction proceeds at a constant temperature, rather than the PCR method, which requires a temperature cycle of increasing/ decreasing the temperature, the present invention can be applied to simple detection methods. Moreover, by staining with a detection reagent that does not show luminescence for normal single-stranded nucleic acid (DNA or RNA) or double-stranded nucleic acid (DNA/DNA, DNA/RNA, or RNA/RNA), such as ThT (derivative), a detection reagent-binding sequence such as a guanine quadruplex-containing sequence generated can be specifically detected by fluorescence or the like.

BRIEF DESCRIPTION OF THE DRAWINGS

FIG. 3-1 shows diagrams (halftone pictures) showing fluorescence spectra of ThT observed upon mixing with various oligonucleotides in TRS50K (A), PBS150K (B), PBS140KM (C), or PBS153NM (D).

FIG. 3-2 shows diagrams (halftone pictures) showing fluorescence spectra of ThT-DB observed upon mixing with various oligonucleotides in TRS50K (A), PBS150K (B), PBS140KM (C), or PBS153NM (D).

FIG. 3-3 shows diagrams (halftone pictures) showing fluorescence spectra of ThT-HE observed upon mixing with various oligonucleotides in TRS50K (A), PBS150K (B), PBS140KM (C), or PBS153NM (D).

FIG. 3-4 shows diagrams (halftone pictures) showing relative fluorescence intensities of ThT for dsDNA observed upon mixing with various oligonucleotides in PBS150K (A) or PBS153NM (B).

FIG. 3-5 shows diagrams (halftone pictures) showing relative fluorescence intensities of ThT-DB for dsDNA observed upon mixing with various oligonucleotides in PBS150K (A) or PBS153NM (B).

FIG. 3-6 shows diagrams (halftone pictures) showing relative fluorescence intensities of ThT-HE for dsDNA observed upon mixing with various oligonucleotides in PBS150K (A) or PBS153NM (B).

FIG. 4 shows a diagram showing the sequences of the target RNA, single-stranded circular DNA template, and primers in Example 1.

FIG. 5 shows diagrams (photographs) showing the results of detection of target RNA in Examples. (A) Use of SYBR Gold (trademark) as a dye. (B) Use of a ThT derivative as a dye. The compositions of the reaction liquids correspond to those in Table 2.

FIG. 6 shows a diagram showing the sequences of the target RNA, single-stranded circular DNA template, and primers in Example 2.

EMBODIMENTS FOR CARRYING OUT THE INVENTION

Detection Kit: First Embodiment

Figure 1:
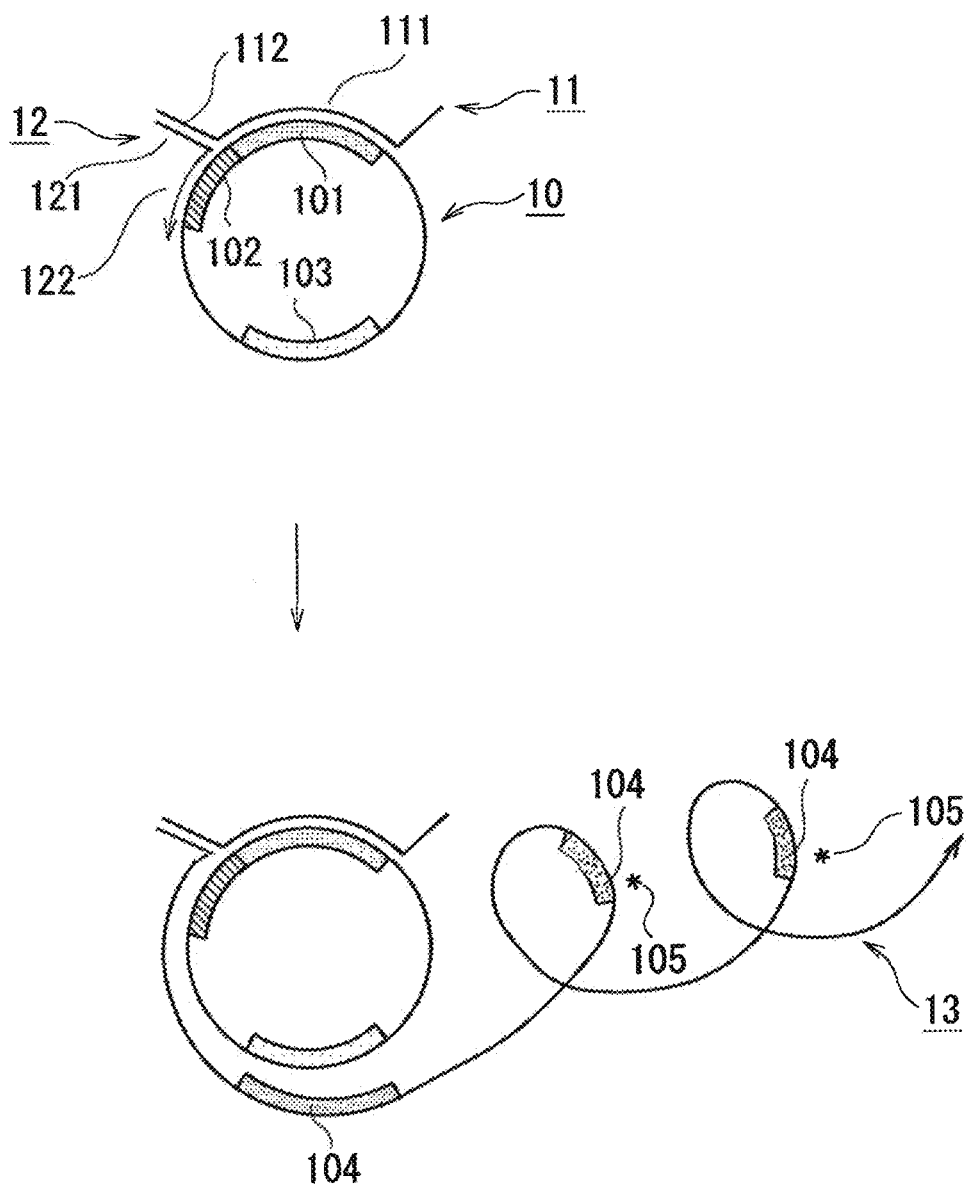
FIG. 1 shows a schematic diagram illustrating the RNA detection method according to the first embodiment of the present invention.

The target RNA detection kit according to the first embodiment of the present invention comprises:
(i) a single-stranded circular DNA template containing:
    a sequence of 10 to 30 bases complementary to a first portion of a target RNA;
    a primer-binding sequence of 7 to 8 bases adjacent to 5'-side thereof; and
    a sequence complementary to a detection reagent-binding sequence such as a guanine quadruplex-forming sequence;
(ii) an oligonucleotide primer containing:
    a sequence of 8 to 15 bases complementary to a second portion adjacent to the 3'-side of the first portion of the target RNA; and
    a sequence of 7 to 8 bases adjacent to 3'-side thereof and complementary to the primer-binding sequence of the single-stranded circular DNA template; and
(iii) a detection reagent such as a guanine quadruplex-binding reagent.

<Target RNA>

The target RNA is not limited. Any kind of RNA such as mRNA, ribosomal RNA (rRNA), or transfer RNA (tRNA) may be detected as a target. The mRNA to be detected may have or may not have a poly A sequence. The RNA may be a non-coding RNA such as siRNA, miRNA, piRNA, rasiRNA, rRNA, or tRNA, or may be genomic RNA of a virus or the like. The RNA to be detected may have either a linear form or a circular form. Examples of the RNA include RNA which is expressed specifically in a disease, RNA whose expression level changes in a disease, and RNA of a virus or a pathogen that causes a disease such as an infection, or causes a toxicosis.

The target RNA may be prepared or isolated from a sample derived from a biological species. As a sample containing such RNA, the individual itself of a virus, or of a prokaryote or eukaryote, or a part thereof may be used. In cases of vertebrates (including human), examples of the sample include excrements such as feces, urine, and sweat; and body fluids such as blood, semen, saliva, gastric juice, and bile. The sample may also be a tissue surgically removed from a body, or a tissue dropped from a body such as a body hair. The sample may also be a prepared RNA-containing product that is prepared from a processed product of food or the like. The sample may also be an RNA-containing product prepared from a sample obtained by separating a part of the above sample by further carrying out fractionation. The RNA to be targeted which is contained in the sample may be either purified or unpurified. From the viewpoint of avoiding degradation of the RNA of interest, the sample may be a sample having decreased ribonuclease activity. For example, the sample may be a sample prepared by treatment with a ribonuclease inhibitor to suppress ribonuclease activity.

The length of the target RNA is also not limited as long as it can hybridize with the single-stranded circular DNA template and the primer. Since hybridization of the single-stranded circular DNA template easily occurs in the loop portion of a stem-loop structure, the RNA preferably has a stem-loop structure.

<Single-Stranded Circular DNA Template>

The single-stranded circular DNA template contains:
  a sequence of 10 to 30 bases complementary to a first portion of a target RNA;
  a primer-binding sequence of 7 to 8 bases adjacent to 5'-side thereof; and
  a sequence complementary to a detection reagent-binding sequence such as a guanine quadruplex-forming sequence.

A description is given below with reference to FIG. 1. The single-stranded circular DNA template is illustrated in the 5' to 3' clockwise direction. The single-stranded circular DNA template 10 contains:
  the sequence 101 which is complementary to the first portion 111 of the target RNA 11;
  the primer-binding sequence 102 which is linked to 5'-side of the sequence 101; and
  the sequence 103 which is complementary to a guanine quadruplex-forming sequence.

The sequence 101 has a length of usually 10 to 30 bases, preferably 15 to 25 bases, and a GC content of preferably 30 to 70%. The sequence 102 has a length of 7 bases or 8 bases. The sequence is not limited, and has a GC content of preferably 30 to 70%.

Examples of the guanine quadruplex-forming sequence include a sequence described in Nat Rev Drug Discov. 2011 April; 10(4): 261-275, and can be represented as $G_3N_{1-10}G_3N_{1-10}G_3N_{1-10}G_3$. Specific examples of the sequence include the sequences of SEQ ID NOs:1 to 6. Accordingly, examples of the sequence complementary to the guanine quadruplex-forming sequence include $C_3N_{1-10}C_3N_{1-10}C_3N_{1-10}C_3$. That is, in the sequence, three consecutive C's are repeated four times via spacers each having a sequence composed of one to ten (preferably one to five) arbitrary bases (N=A, T, G, or C).

The sequence complementary to the guanine quadruplex-forming sequence may have arbitrary sequences before and after it, that is, between it and the primer-binding sequence 102, and between it and the sequence 101 which is complementary to the first portion of the target RNA. The total length of the single-stranded circular DNA template 10 is preferably 35 to 100 bases.

Although FIG. 1 describes a case where the detection reagent-binding sequence is a guanine quadruplex-forming sequence, the detection may also be carried out using as a detection reagent-binding sequence an aptamer sequence or a molecular beacon (hairpin-shaped oligonucleotide having a fluorescent group (donor) and a quenching group (acceptor) that cause FRET)-binding sequence, and using as a detection reagent an aptamer-binding coloring molecule or a molecular beacon.

The single-stranded circular DNA template 10 can be obtained by circularization of a single-stranded DNA (ss-DNA). The circularization of the single-stranded DNA can be carried out by arbitrary means. It can be carried out by using, for example, CircLigase (registered trademark), CircLigase II (registered trademark), ssDNA Ligase (Epicentre), or ThermoPhage ligase (registered trademark) single-stranded DNA (Prokzyme).

<Oligonucleotide Primer>

The primer 12 contains: a sequence of 8 to 15 bases (sequence 121) which is complementary to the second portion 112 adjacent to the 3'-side of the first portion 111 of the target RNA 11; and a sequence of 7 to 8 bases (sequence 122) which is linked to the 3'-side of the sequence 121 and complementary to the primer-binding portion 102 of the single-stranded circular DNA template 10. The primer may be immobilized by, for example, immobilization on a carrier. By this, detection on the solid phase can also be carried out. Examples of the method of the immobilization include a method in which the primer is labeled with biotin or the like, and then immobilized by interaction with avidin or the like.

<Amplification Method>

After hybridizing the single-stranded circular DNA template 10 and the primer 12 with the target RNA 11 to allow formation of a complex of these three molecules, nucleic acid amplification reaction based on the target RNA is carried out using a rolling circle amplification (RCA) method.

Those skilled in the art can appropriately set the conditions for the hybridization taking into account the combination of the single-stranded circular DNA template, the target RNA, and the primer.

The RCA method is described in, for example, Lizardi et al., Nature Genet. 19: 225-232 (1998); U.S. Pat. Nos. 5,854,033 B; 6,143,495 B; and WO 97/19193. The RCA method can be carried out using a mesophilic chain-substituting DNA synthetase such as phi29 polymerase, Klenow DNA Polymerase (5'-3', 3'-5' exo minus), Sequenase (registered trademark) Version 2.0 T7 DNA Polymerase (USB), Bsu DNA Polymerase, or Large Fragment (NEB); or a heat-resistant chain-substituting DNA synthetase such as Bst DNA Polymerase (Large Fragment), Bsm DNA Polymerase, Large Fragment (Fermentas), BcaBEST DNA polymerase (TakaraBio), Vent DNA polymerase (NEB), Deep Vent DNA polymerase (NEB), or DisplaceAce (registered trademark) DNA Polymerase (Epicentre).

The extension reaction of DNA by RCA does not require use of a thermal cycler, and is carried out, for example, at a constant temperature within the range of 25° C. to 65° C. The reaction temperature is appropriately set according to a normal procedure based on the optimum temperature of the enzyme and the denaturation temperature (the temperature range in which binding (annealing) of the primer to, or dissociation of the primer from, the template DNA occurs), which is dependent on the primer chain length. The reaction may also be carried out at a constant, relatively low temperature. For example, in cases where phi29DNA polymerase is used as the chain-substituting DNA synthetase, the reaction is carried out preferably at 25° C. to 42° C., more preferably at about 30 to 37° C. By the RCA, nucleic acid (amplification product 13) containing a guanine quadruplex-forming sequence (corresponding to the sequence 103) is amplified dependently on the target RNA 11 from the primer 12 along the single-stranded circular DNA template 10.

Since the amplification product 13 contains a sequence containing a guanine quadruplex 104, it can be detected with a guanine quadruplex detection reagent 105.

Detection Kit: Second Embodiment

The target RNA detection kit according to the second embodiment of the present invention comprises:
(i) a first single-stranded circular DNA template containing:
   a sequence of 10 to 30 bases complementary to a first portion of a target RNA;
   a first primer-binding sequence of 7 to 8 bases adjacent to 5'-side thereof; and
   a second single-stranded circular DNA-binding sequence;
(ii) a first oligonucleotide primer containing:
   a sequence of 8 to 15 bases complementary to a second portion adjacent to the 3'-side of the first portion of the target RNA; and
   a sequence of 7 to 8 bases adjacent to 3'-side thereof and complementary to the first primer-binding portion of the first single-stranded circular DNA template;
(iii) a second single-stranded circular DNA containing:
   the same sequence as the second single-stranded circular DNA-binding sequence of the first single-stranded circular DNA;
   a second primer-binding sequence adjacent to 3'-side thereof; and
   a sequence complementary to a detection reagent-binding sequence such as a guanine quadruplex-forming sequence;
(iv) a second oligonucleotide primer containing:
   the same sequence as the portion adjacent to the 5'-side of the second single-stranded circular DNA-binding sequence of the first single-stranded circular DNA; and
   a sequence adjacent to 3'-side thereof and complementary to the second primer-binding sequence of the second single-stranded circular DNA; and
(v) a detection reagent such as a guanine quadruplex-binding reagent.

<Target RNA>

The target RNA is as described for the first embodiment.

<First Single-Stranded Circular DNA Template>

The first single-stranded circular DNA template contains:
a sequence of 10 to 30 bases complementary to a first portion of a target RNA;
a primer-binding sequence of 7 to 8 bases adjacent to 5'-side thereof; and
a second single-stranded circular DNA-binding sequence.
A description is given below with reference to FIG. 14.
The first single-stranded circular DNA template 20 contains:
the sequence 201 which is complementary to the first portion 211 of a target RNA 21;
the primer-binding sequence 202 which is linked to 5'-side of the sequence 201; and
the second single-stranded circular DNA-binding sequence 203.

The sequence 201 has a length of usually 10 to 30 bases, preferably 15 to 25 bases, and a GC content of preferably 30 to 70%. The sequence 202 has a length of 7 bases or 8 bases. The sequence is not limited, and has a GC content of preferably 30 to 70%. The total length of the first single-stranded circular DNA template 20 is preferably 35 to 100 bases. The first single-stranded circular DNA template 20 can be obtained by circularization of a single-stranded DNA (ssDNA) by the method described above.

<First Oligonucleotide Primer>

The first oligonucleotide primer 22 contains: a sequence of 8 to 15 bases (sequence 221) which is complementary to the second portion 212 adjacent to the 3'-side of the first portion 211 of the target RNA 21; and a sequence of 7 to 8 bases (sequence 222) which is linked to 3'-side of the sequence 221 and complementary to the primer-binding portion 202 of the first single-stranded circular DNA template 20.

<Second Single-Stranded Circular DNA Template>

The second single-stranded circular DNA template 24 contains:
the sequence 241 which has the same sequence as the second single-stranded circular DNA-binding sequence 203 of the first single-stranded circular DNA 20;
the second primer-binding sequence 242 which is adjacent to 3'-side of the sequence 241; and
the sequence 243 which is complementary to a guanine quadruplex-forming sequence.

The sequence 241 has a length of usually 10 to 30 bases, preferably 15 to 25 bases, and a GC content of preferably 30 to 70%. The sequence 242 has a length of 7 bases or 8 bases. The sequence is not limited, and has a GC content of preferably 30 to 70%. The sequence 243 complementary to a guanine quadruplex-forming sequence is the same as that described for the first embodiment. The total length of the second single-stranded circular DNA template 24 is preferably 35 to 100 bases. The second single-stranded circular DNA template 24 can be obtained by circularization of a single-stranded DNA (ssDNA) by the method described above.

Figure 14:
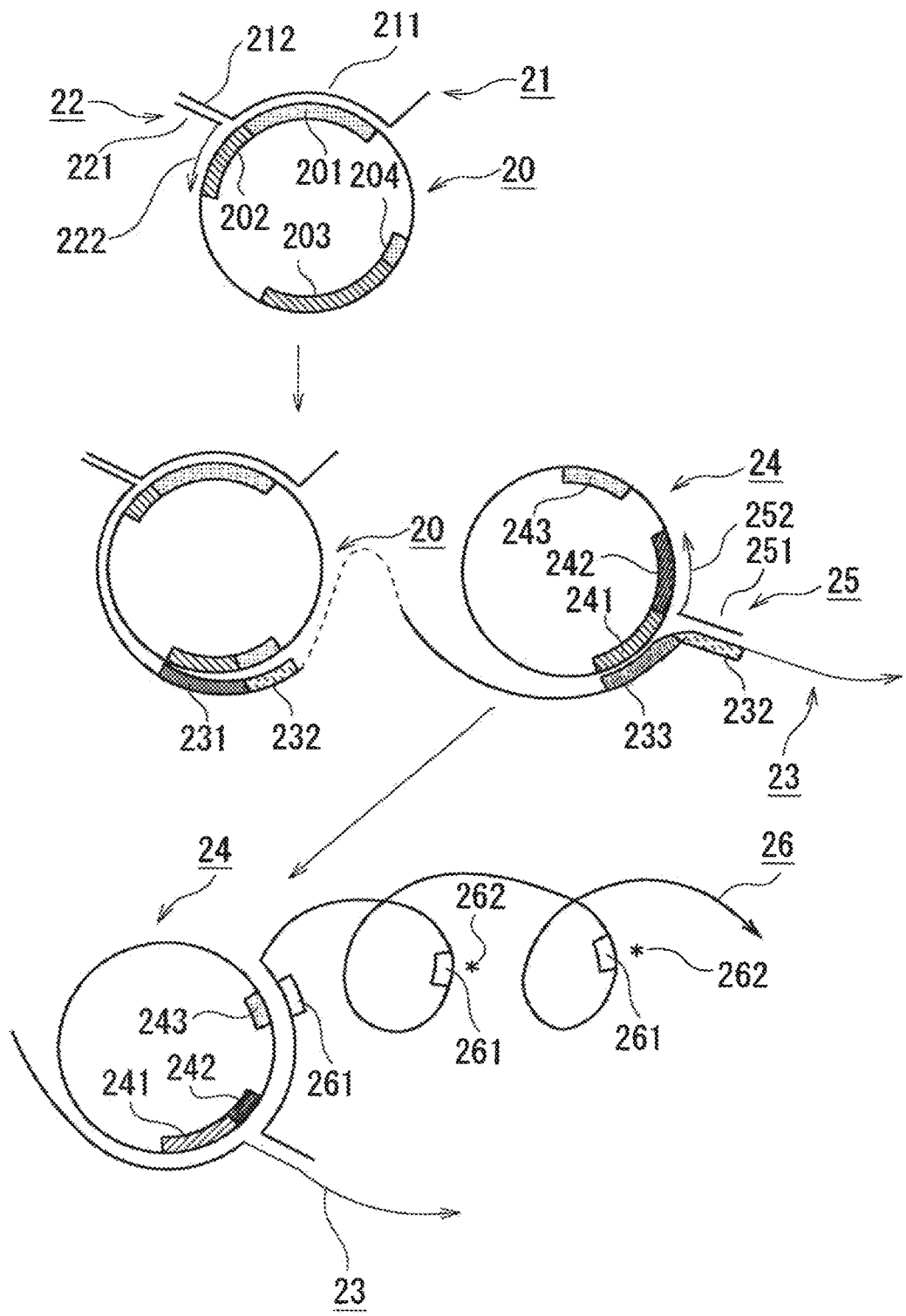
FIG. 14 shows a schematic diagram illustrating the RNA detection method according to the second embodiment of the present invention.

Although FIG. 14 describes a case where the detection reagent-binding sequence is a guanine quadruplex-forming sequence, the detection may also be carried out using as a detection reagent-binding sequence an aptamer sequence or a molecular beacon (hairpin-shaped oligonucleotide having a fluorescent group (donor) and a quenching group (acceptor) that cause FRET)-binding sequence, and using as a detection reagent an aptamer-binding coloring molecule or a molecular beacon (ChemBioChem 2007, 8, 1795-1803; J. Am. Chem. Soc. 2013, 135, 7430-7433).

<Second Oligonucleotide Primer>

The second oligonucleotide primer 25 contains:
the sequence 251 which has the same sequence (preferably sequence of 8 to 15 bases) as the portion 204 adjacent to the 5'-side of the second single-stranded circular DNA-binding sequence 203 of the first single-stranded circular DNA 20; and
the sequence 252 (preferably sequence of 7 to 8 bases) which is adjacent to the 3'-side of the sequence 251 and complementary to the second primer-binding sequence 242 of the second single-stranded circular DNA.

<Amplification Method>

As shown in FIG. 14, after hybridizing the first single-stranded circular DNA template 20 and the primer 22 with the target RNA 21 to allow formation of a complex of these three molecules, nucleic acid amplification reaction based on the target RNA is carried out using a rolling circle amplification (RCA) method. The reaction conditions and the like are the same as those for the first embodiment.

By the RCA, a first amplification product 23 is amplified dependently on the target RNA 21 from the primer 22 along the first single-stranded circular DNA template 20.

Since the amplification product 23 contains the sequence 231 which is complementary to the second single-stranded circular DNA-binding sequence 203 of the first single-stranded circular DNA template 20, the second single-stranded circular DNA 24, which contains the same sequence (sequence 241) as the sequence 203, hybridizes with the sequence 231 of the first amplification product 23 via the sequence 241.

With the thus formed complex of the first amplification product 23 and the second single-stranded circular DNA, the second oligonucleotide primer 25 hybridizes to form a complex of these three molecules.

That is, since the second oligonucleotide primer 25 contains the same sequence (sequence 251) as the portion 204 adjacent to the 5'-side of the second single-stranded circular DNA-binding sequence 203 of the first single-stranded circular DNA 20, the second oligonucleotide primer 25 hybridizes with the region 232 of the first amplification product 23, which region is complementary to the portion 204 of the first single-stranded circular DNA 20, via the sequence 251.

Since the second oligonucleotide primer 25 contains, in the 3'-side of the sequence 251, the sequence 252 which is complementary to the second primer-binding sequence 242 of the second single-stranded circular DNA 24, the second oligonucleotide primer 25 also hybridizes with the second single-stranded circular DNA 24 via the sequence 252.

By RCA, a second amplification product 26 is amplified from the resulting complex of the first amplification product 23, second single-stranded circular DNA 24, and second oligonucleotide primer 25. Since the second amplification product 26 contains a sequence 261 containing a guanine quadruplex, it can be detected with a guanine quadruplex detection reagent 262. In the second embodiment, the second single-stranded circular DNA 24 hybridizes with each region 231 contained in the first amplification product 23 to cause RCA reaction. Thus, a remarkable improvement in the detection sensitivity can be achieved.

<Detection Method>

Since, in both the first and second embodiments, the amplification product obtained by RCA contains a guanine quadruplex, the amplification product can be detected using a guanine quadruplex-binding reagent. Examples of the guanine quadruplex-binding reagent include the following reagents.

[1] Thioflavin T (ThT) or a derivative thereof

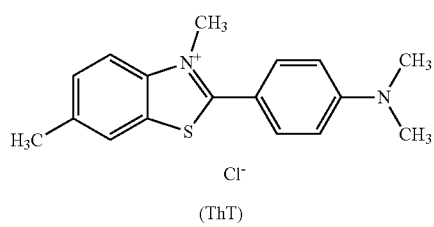

(ThT)

[2] H-aggregate "Yan, J. W.; Ye, W. J.; Chen, S. B.; Wu, W. B.; Hou, J. Q.; Ou, T. M.; Tan, J. H.; Li, D.; Gu, L. Q.; Huang, Z. S. Anal. Chem. 2012, 84, 6288-6292."

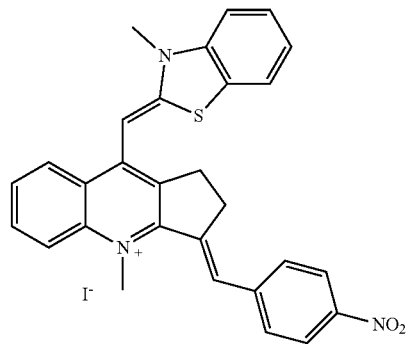

[3] TMPyP4 "Yaku, H.; Fujimoto, T.; Murashima, T.; Miyoshi, D.; Sugimoto, N. Chem. Commun. 2012, 48, 6203-6216."

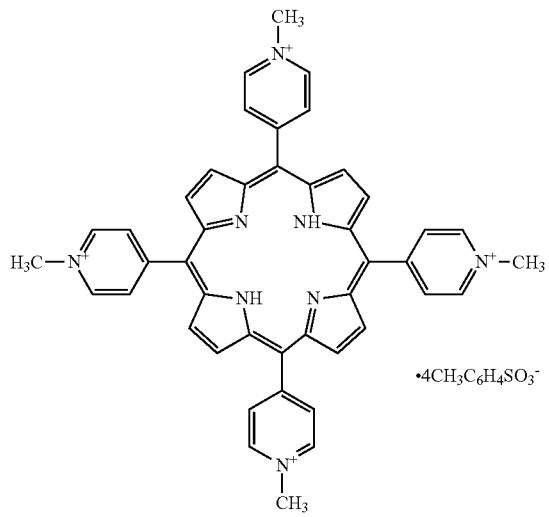

[4] PPIX "Li, T.; Wang, E.; Dong, S. Anal. Chem. 2010, 82, 7576-7580."

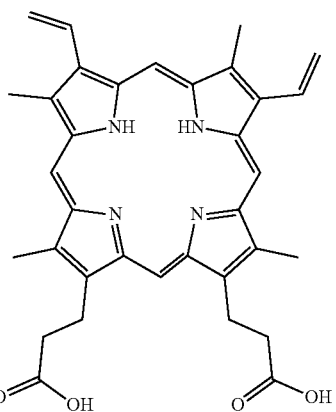

[5] BPBC "Jin, B.; Zhang, X.; Zheng, W.; Liu, X.; Qi, C.; Wang, F.; Shangguan, D. Anal. Chem. 2014, 86, 943-952."

[6] APD "Nikan, M.; Di Antonio, M.; Abecassis, K.; McLuckie, K.; Balasubramanian, S. Angew. Chem., Int. Ed. 2013, 52, 1428-1431."

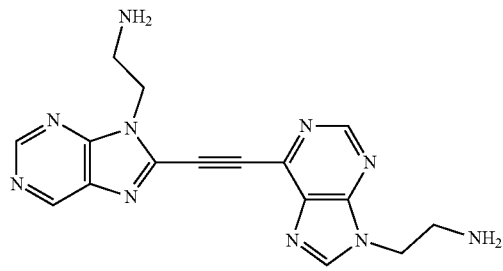 [SMILES: NCCn1cnc2c(C#Cc3nc4cncnc4n3CCN)ncnc21]

[7] Thiazole Orange (TO)
"Nakayama S.; Kelsey I.; Wang J.; Roelofs K.; Stefane B.; Luo Y.; Lee V. T.; Sintim H. O. J. Am. Chem. Soc. 2011, 133, 4856-4864."

Preferably, a ThT derivative represented by the following General Formula (I) may be used (Anal. Chem. 2014, 86, 12078-12084).

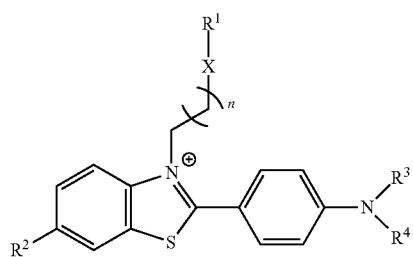

In this formula, $R^1$ represents hydrogen, or a $C_1$-$C_{10}$ (preferably $C_1$-$C_5$) hydrocarbon group which optionally contains one or more selected from the group consisting of O, S, and N. The hydrocarbon group may be either linear or branched, or either saturated or unsaturated. The hydrocarbon group may be an aliphatic hydrocarbon group such as an alkyl group, or may be an aromatic hydrocarbon group such as an aryl group or an arylalkyl group. The term "optionally contains one or more selected from the group consisting of O, S, and N" means that the hydrocarbon group may contain a functional group containing a nitrogen atom, oxygen atom, sulfur atom, or the like, such as an amino group (—$NR_2$) (wherein each R independently represents hydrogen or a $C_1$-$C_5$ alkyl group), nitro group (—$NO_2$), cyano group (—CN), isocyanate group (—NCO), hydroxyl group (—OH), aldehyde group (—CHO), carboxyl group (—COOH), mercapto group (—SH), or sulfonic acid group (—$SO_3H$), or that a linking group containing a nitrogen atom, oxygen atom, sulfur atom, or the like, such as an ether group (—O—), imino group (—NH—), thioether group (—S—), carbonyl group (—C(=O)—), amide group (—C(=O)—NH—), ester group (—C(=O)—O—), or thioester group (—C(=O)—S—), may be contained in the inside or at a terminus of the carbon backbone of the hydrocarbon group.

$R^2$, $R^3$, and $R^4$ each independently represent a $C_1$-$C_5$ (aliphatic) hydrocarbon group, more preferably a $C_1$-$C_3$ hydrocarbon group, especially preferably a methyl group. The $C_1$-$C_5$ hydrocarbon group may be either linear or branched, or either saturated or unsaturated.

n represents an integer of 0 to 5, more preferably an integer of 0 to 3, especially preferably 1.

X represents O, S, or NH, more preferably 0.

Specific examples of the compound include the following.

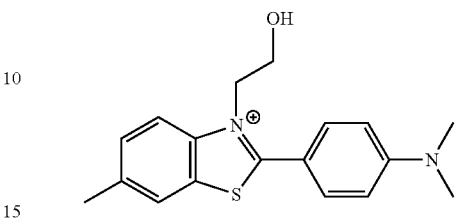

ThT-HE

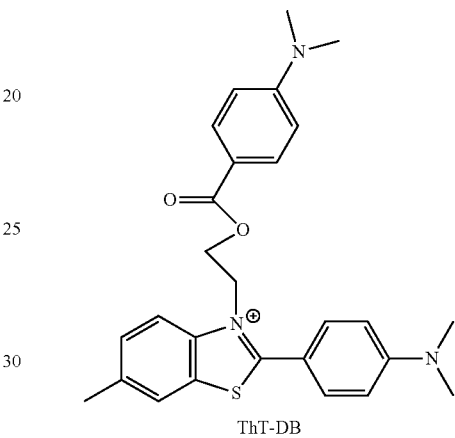

ThT-DB

The detection of the guanine quadruplex structure in the test DNA can be carried out by, for example, bringing a compound represented by General Formula (I) or a salt thereof into contact with a sample containing the RCA product, and detecting the compound bound to the guanine quadruplex structure based on fluorescence emitted from the compound. The detection operation itself is the same as a known method except that a compound represented by General Formula (I) or a salt thereof is used. The detection operation can be carried out by bringing a solution prepared by dissolving the compound in a buffer into contact with a sample containing a test DNA, incubating the resulting mixture, carrying out washing, and then detecting fluorescence from a fluorescent dye bound to the test DNA after the washing.

Reference Example

For showing examples of guanine quadruplex detection reagents that may be used in the method of the present invention, examples of synthesis of ThT derivatives and examples of experiments for detection of a guanine quadruplex using the ThT derivatives are shown below.

1. Apparatus and the Like

NMR spectra were measured using JNM-ECS400 and JNM-ECA600 (JEOL LTD., Tokyo, Japan). ESI mass spectra were measured using an API2000 mass spectrometer (Applied Biosystems, Tokyo, Japan). Fluorescence spectra were measured using an LS-55 fluorescence spectrophotometer (Perkin Elmer Japan Co., Ltd., Kanagawa, Japan).

2. Materials

2-Amino-6-methylbenzothiazole, 3,4-dihydro-2H-pyran (DHP), methyl bromoacetate, pyridinium p-toluenesulfonic acid (PPTS), and sodium borohydride (NaBH4) were purchased from Tokyo Chemical Industry Co., Ltd. (Tokyo, Japan). Silica gel 60 and trifluoroacetic acid (TFA) were purchased from Kanto Chemical Co., Inc. (Tokyo, Japan). Acetonitrile (MeCN), ammonium chloride, dichloromethane ($CH_2Cl_2$), diethylether, dipotassium hydrogen phosphate ($K_2HPO_4$), disodium hydrogenphosphate ($Na_2HPO_4$), ethanol (EtOH), ethylene glycol, hydrochloric acid (aqueous HCl solution), magnesium chloride hexahydrate ($MgCl_2 \cdot 6H_2O$), magnesium sulfate heptahydrate, methanol (MeOH), potassium chloride (KCl), potassium dihydrogen phosphate ($KH_2PO_4$), potassium hydroxide (KOH), sodium chloride (NaCl), sodium dihydrogen phosphate dihydrate ($NaH_2PO_4 \cdot 2H_2O$), sodium sulfate ($Na_2SO_4$), and thioflavin T (ThT) were purchased from Wako Pure Chemical Industries, Ltd. (Osaka, Japan). Calf thymus DNA (deoxyribonucleic acid derived from calf thymus, XV type), 4-(dimethylamino)benzoyl chloride, and Trizma (registered trademark) base were purchased from Sigma-Aldrich, Inc. (Missouri, USA). Oligonucleotides were purchased from Japan Bio Services Co., LTD. (Saitama, Japan) and GeneDesign Inc. (Osaka, Japan).

3. Synthesis of Thioflavin T Derivatives

The present inventors focused on four methyl groups as candidate substitution sites in ThT. Based on molecular dynamics (MD) simulation, it was suggested that only the methyl group at N3 position of the benzothiazole ring significantly overlaps with the G-quartet plane. Accordingly, the present inventors considered that introduction of a substituent to this position may improve specificity for distinguishing different G4 types.

First, in view of this, ThT-DB and ThT-HE were synthesized from 2-amino-6-methylbenzothiazole by a 7-step reaction.

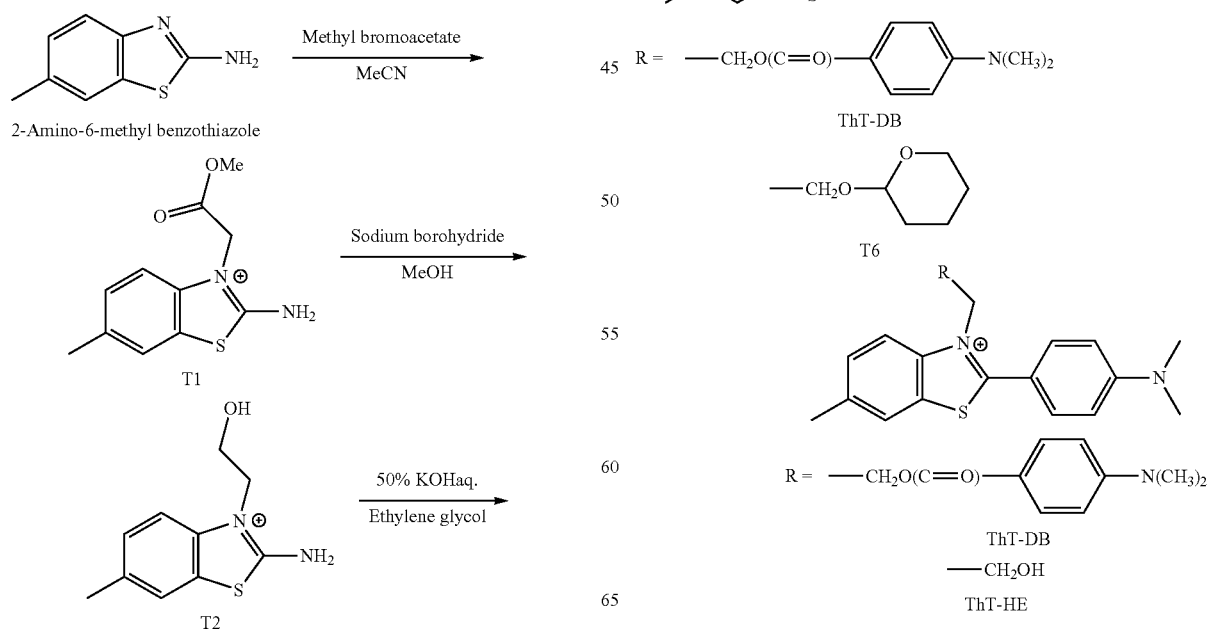

Synthesis of Compound T1:

Methyl bromoacetate (350 μL, 3.7 mmol) was added to a solution of 2-amino-6-methylbenzothiazole (530 mg, 3.3 mmol) in dry MeCN, and the resulting mixture was refluxed for 4 hours. The reaction mixture was dried by evaporation. The resulting residue was suspended in MeCN, and then filtered. The obtained precipitate was dried under vacuum to obtain T1 (837 mg, quantitative yield); $^1$H NMR (400 MHz, methanol-d4) δ 7.63 (1H, s) 7.40-7.33 (2H, q) 5.12 (2H, s) 3.80 (3H, s) 2.41 (3H, s); ESI-MS (cation mode) m/z, Found=237.1, Calcd. for [M$^+$]=237.07.

Synthesis of Compound T2:

NaBH$_4$ (960 mg, 25 mmol) was added to a solution of Compound T1 (502 mg, 2.1 mmol) in dry MeOH (6.8 mL) at 0° C., and the resulting mixture was stirred at room temperature for 24 hours. The reaction mixture was dried by evaporation, and the resulting residue was suspended in ethyl acetate. The resulting suspension was poured into cold water, and the organic layer was washed with water, followed by drying over sodium sulfate. By filtration and subsequent evaporation of the solvent, Compound T2 was obtained as yellow powder (727 mg, 75%); $^1$H NMR (400 MHz, CDCl3) δ 7.09 (1H, s) 7.04-7.02 (1H, d) 6.79-6.77 (1H, d) 4.15-4.13 (2H, t) 3.99-3.96 (2H, t) 2.33 (3H, s); ESI-MS (cation mode) m/z, Found=209.2, Calcd. for [M$^+$]=209.07.

Synthesis of Compound T3:

Compound T2 (711 mg, 3.4 mmol) was added to a mixture of 50% (weight/volume) aqueous KOH solution (47 mL) and ethylene glycol (50 mL), and the resulting reaction mixture was refluxed under argon atmosphere for 24 hours, followed by further stirring the mixture under aeration for 24 hours. The reaction mixture was cooled to room temperature, and then diluted with saturated aqueous ammonium chloride solution, followed by performing extraction with dichloromethane. The resulting organic layer was dried over sodium sulfate, and then filtered. The resulting filtrate was dried by evaporation, and the resulting residue was purified by silica gel column chromatography in a concentration gradient of 0% to 5% methanol in dichloromethane, to obtain Compound T3 as yellow oil (250 mg, 40%); $^1$H NMR (400 MHz, CDCl3) δ 7.11-7.10 (2H, d) 7.07-7.04 (2H, q) 6.60-6.57 (2H, d) 3.72-3.61 (4H, m) 3.28-3.22 (4H, d) 2.17 (6H, s); ESI-MS (cation mode) m/z, Found=365.2, Calcd. for [(M+H)$^+$]=365.53.

Synthesis of Compound T4:

Pyridinium p-toluenesulfonic acid (78 mg, 0.31 mmol) and 3,4-dihydro-2H-pyran (400 μL, 4.7 mmol) were added to a solution of Compound T3 (190 mg, 0.52 mmol) in dry dichloromethane (3.6 mL), and the resulting mixture was stirred at room temperature for 5 hours. The reaction mixture was diluted with diethyl ether. The organic layer was washed with semi-saturated saline to remove catalyst, and then dried over sodium sulfate, followed by drying by evaporation to obtain Compound T4 as yellow oil (276 mg, crude product); ESI-MS (cation mode) m/z, Found=533.3, Calcd. for [(M+H)$^+$]=533.24.

Synthesis of Compound T5:

NaBH$_4$ (224 mg, 5.9 mmol) was added to a solution of crude Compound T4 (158 mg) in dry ethanol (4.7 mL) at 0° C., and the resulting mixture was stirred at room temperature for 8 hours. The reaction mixture was dried by evaporation, and the resulting residue was suspended in ethyl acetate, followed by pouring the resulting suspension into cold water. The organic layer was washed with water, and then dried over sodium sulfate. By filtration and subsequent evaporation of the solvent, Compound T5 was obtained as yellow oil (149 mg, crude product); ESI-MS (cation mode) m/z, Found=268.0, Calcd. for [(M+H)+]=268.12.

Synthesis of ThT-DB and ThT-HE:

4-(dimethylamino)benzoyl chloride (89 mg, 0.48 mmol) was added to a solution of the crude Compound T5 (86 mg) in dry MeCN (2.6 mL), and the resulting mixture was stirred at room temperature for 18 hours. The reaction mixture was diluted with water, and the product was extracted with dichloromethane. The resulting organic layer was dried over sodium sulfate, and then filtered. The resulting filtrate was dried by evaporation, and the resulting residue was purified by silica gel column chromatography in a concentration gradient of 0% to 20% methanol in dichloromethane, to obtain Intermediate T6, and ThT-DB as yellow oil (57 mg, crudely purified product); T6: ESI-MS (cation mode) m/z, Found=397.2, Calcd. for [M$^+$]=397.19; ThT-DB: ESI-MS (cation mode) m/z, Found=460.1, Calcd. for [M$^+$]=460.21. Subsequently, the mixture of T6 and ThT-DB (54 mg) was dissolved in 250 μL of TFA/water/MeOH (2/1/2, volume/volume/volume), and the mixture was stirred at room temperature for 8 hours. The reaction mixture was dried by evaporation, and the resulting residue was purified with an HPLC system equipped with an octadecyl silica (ODS) gel column to obtain each of ThT-HE (2 mg, 1.7% from T4) and ThT-DB (6.8 mg, 5.7% from T4) as yellow powder;

ThT-HE: $^1$H NMR (600 MHz, CDCl3) δ 8.13-8.12 (1H, d) 7.90-7.89 (2H, d) 7.73 (1H, s) 7.62-7.61 (1H, d) 6.86-6.85 (2H, d) 4.94 (2H, s) 4.37 (2H, s) 3.16 (6H, s) 2.57 (3H, s); ESI-MS (cation mode) m/z, Found=313.1, Calcd. for [M$^+$]=313.14;

ThT-DB: $^1$H NMR (600 MHz, CDCl3) δ 8.20-8.19 (1H, d) 7.79 (1H, s) 7.70-7.69 (2H, d) 7.61-7.60 (1H, d) 7.55-7.54 (2H, d) 6.75-6.74 (2H, d) 6.53-6.52 (2H, d) 5.49 (2H, s) 4.74 (2H, s) 3.12 (6H, s) 3.04 (6H, s) 2.55 (3H, s); ESI-MS (cation mode) m/z, Found=460.1, Calcd. for [M$^+$]=460.21.

4. Evaluation of THT Derivatives

Subsequently, fluorescence properties of ThT and ThT derivatives, and compound-induced topology changes in G4 were investigated under conditions where various G4-forming oligonucleotides are present.

The following six kinds of G4-forming human-derived oligonucleotides were used:

```
22mer DNA
(22AG: 5'-AGGGTTAGGGTTAGGGTTAGGG-3' (SEQ ID NO: 1)
and

22Kit:
5'-AGGGAGGGCGCTGGGAGGAGGG-3' (SEQ ID NO: 2));

26mer DNA
(26Tel: 5'-TTAGGGTTAGGGTTAGGGTTAGGGTT-3' (SEQ ID
NO: 3));

27mer DNA
(27Myc: 5'-TGGGGAGGGTGGGAGGGTGGGGA AGG-3' (SEQ ID
NO: 4));

20mer DNA
(20Src: 5'-GGGCGGCGGGCTGGGCGGGG-3' (SEQ ID NO: 5));
and

18mer RNA
(18Ras: 5'-GGGAGGGGCGGGUCUGGG-3' (SEQ ID NO: 6)).
```

These were obtained from human genes:
telomere regions (22AG and 26Tel);
the nuclease-sensitive element region of the c-Myc P1 promoter (27Myc);
the 87-nucleotide upstream region of the transcription initiation site of a proto-oncogene encoding tyrosine kinase (22Kit);
a proto-oncogene encoding a nonreceptor tyrosine kinase (20Src); and
the 5'-untranslated region of a human NRAS proto-oncogene transcript (18Ras).

Besides these sequences, the following two kinds of oligonucleotides were used as standards:

```
17mer DNA
(ssDNA: 5'-GGGTTACTACGAACTGG-3' (SEQ ID NO: 7));
and complementary sequence of ssDNA
(cDNA: 5'-CCAGTTCGTAGTAACCC-3' (SEQ ID NO: 8)).
```

The ssDNA was used as a single-stranded DNA, and the cDNA was used as a double-stranded DNA (dsDNA) by mixing with the ssDNA at a ratio of 1:1.

In order to analyze the effect of buffering conditions on the spatial structure of G4, and its effect on fluorescence radiation, four kinds of buffer solutions were used:

TRS50K (50 mM Tris-HCl, 50 mM KCl; pH 7.2);
PBS150K (92 mM $HPO_4^{2-}$, 150 mM $K^+$, 15 mM $Nat$; pH 7.0);
PBS140KM (80 mM $HPO_4^{2-}$, 2.5 mM $SO4^{2-}$, 140 mM $K^+$, 10 mM $Nat$, 2.5 mM $Mg^{2+}$; pH 7.4); and
PBS153NM (10 mM $HPO_4^{2-}$, 146 mM $Cl^-$, 153 mM $Nat$, 2.7 mM $K^+$, 2.5 mM $Mg^{2+}$; pH7.4).

PBS150K and PBS140KM are similar to intracellular ionic components, and PBS153NM is a typical phosphate physiological saline.

4-1. Fluorescence Spectrum Analysis

Each of the eight kinds of oligonucleotides (22AG, 26Tel, 27Myc, 22Kit, 20Src, 18Ras, ssDNA, and dsDNA) was dissolved in the buffer TRS50K, PBS150K, PBS140KM, or PBS153NM at a concentration of 21 μM, and denatured by heating at 95° C. (or at 40° C. for 18Ras) for 0.5 minute using a thermal cycler, followed by cooling the resulting solution to 25° C. at a rate of 0.5° C./minute to allow refolding. Each solution was diluted to an appropriate oligonucleotide concentration, and its aliquots (50 μL each) were incubated at 25° C. for 30 minutes, followed by mixing each aliquot with 20 μL of a solution of a dye (ThT, ThT-DB, or ThT-HE; 10.5 μM) in the buffer TRS50K, PBS150K, PBS140KM, or PBS153NM. These mixtures were incubated at 25° C. for 30 minutes. An emission spectrum of each dye was obtained by excitation at 415 nm and monitoring of fluorescence between 450 nm and 600 nm.

Figure 2:
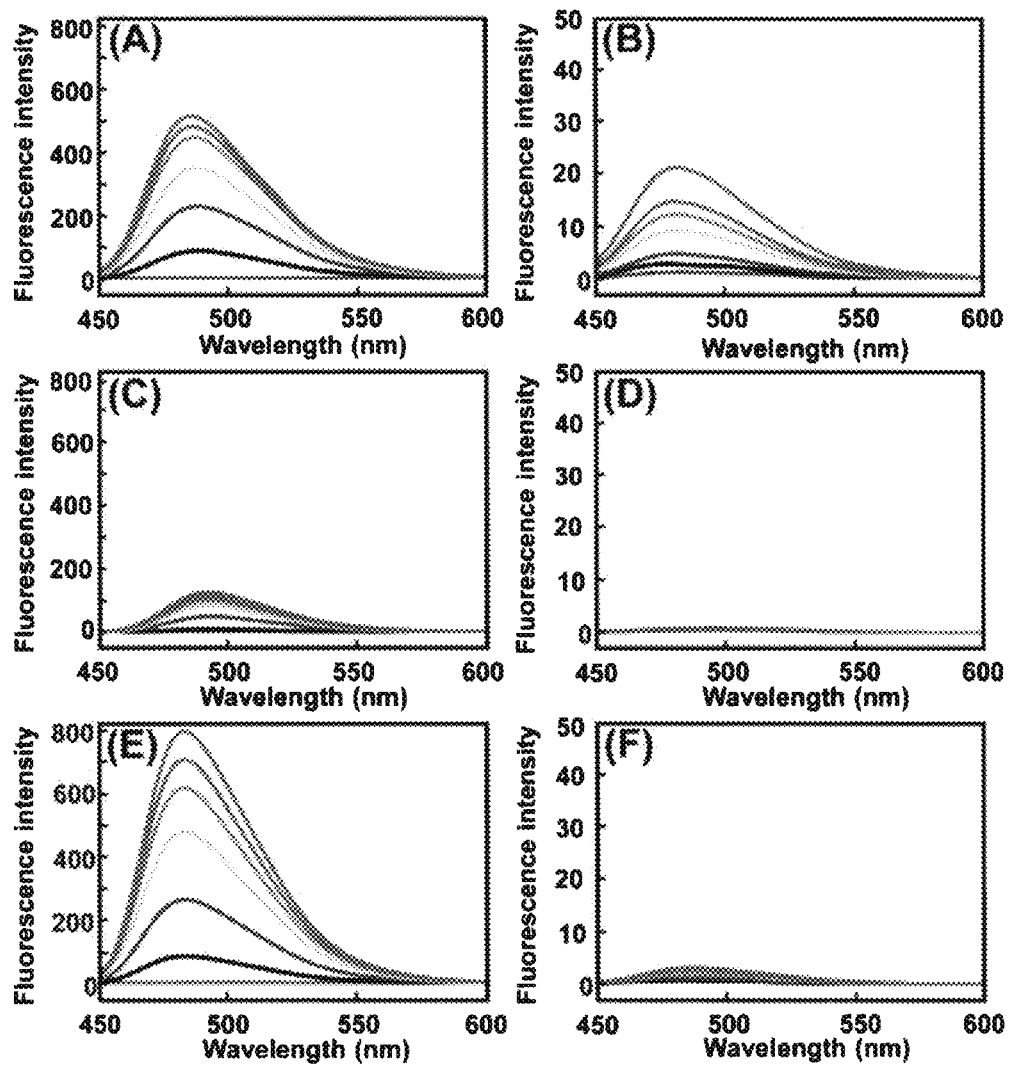
FIG. 2 shows diagrams (halftone pictures) showing fluorescence spectra of ThT (A and B), ThT-DB (C and D), and ThT-HE (E and F) (3 µM) in PBS153NM which were observed at increasing concentrations (0, 1, 3, 6, 9, 12, and 15 µM) of 27Myc (A, C, and E) or dsDNA (B, D, and F). Oligonucleotide concentrations: 0 µM (purple), 1 µM (black), 3 µM (blue), 6 µM (light blue), 9 µM (green), 12 µM (yellow), and 15 µM (red).
Figures 1, 3:
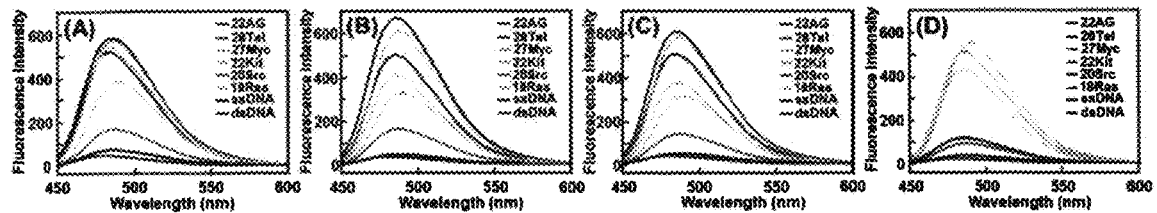
Figures 2, 3:
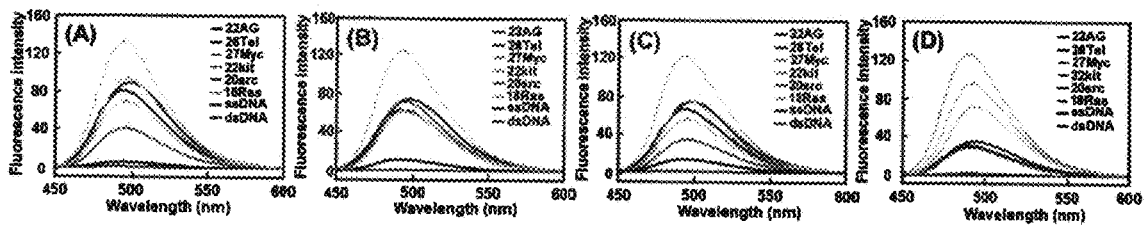
Figure 3:
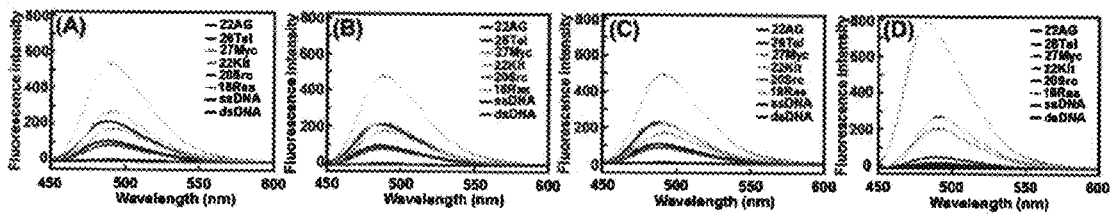

FIG. 2 shows the results obtained by mixing ThT, ThT-DB, or ThT-HE with 27Myc or dsDNA. FIGS. 3-1 to 3-3 show the results obtained by mixing ThT, ThT-DB, or ThT-HE with various oligonucleotides in various buffers.

From FIG. 2, it was found that ThT shows a considerable level of emission of fluorescence even in the presence of dsDNA, resulting in high background, while ThT-DB and ThT-HE hardly show fluorescence in the presence of dsDNA and hence have high specificity to guanine quadruplex.

FIGS. 3-4 to 3-6 show relative fluorescence intensities as the peaks of the emitted light at 485 nm (ThT and ThT-HE) or 500 nm (ThT-DB) with respect to the intensity of the dye that interacted with dsDNA, which was taken as 1. The X-axis represents the oligonucleotide concentration.

The Kd values were determined based on the titration curves in FIGS. 3-4 to 3-6, and are shown in Table 1.

According to the results in Table 1, affinity of ThT-HE to the target G4 was found to be generally lower than affinity of ThT to the target G4. However, ThT-DB showed almost the same level of affinity to the target G4.

TABLE 1

Binding of ThT and derivatives to target oligonucleotides

| dye | buffer | $K_d$ (μM)a 22AG | 26Tel | 27Mye | 22Kit | 20Sre | 18Ras | ssDNA | dsDNA |
|---|---|---|---|---|---|---|---|---|---|
| ThT | PBS150K | 7.3 ± 0.3 | 5.0 ± 0.8 | 8.7 ± 1.0 | 12.3 ± 1.8 | n.d. | 10.3 ± 3.0 | n.d. | n.d. |
|  | PBS153NM | n.d. | 25.3 ± 1.5 | 7.2 ± 0.6 | 7.2 ± 0.9 | n.d. | 16.0 ± 4.2 | n.d. | n.d. |
| ThT-DB | PBS150K | 4.5 ± 0.4 | 2.1 ± 0.3 | 6.7 ± 0.7 | 16.0 ± 1.7 | 22.0 ± 1.5 | 11.8 ± 1.8 | n.d. | n.d. |
|  | PBS153NM | n.d. | 5.1 ± 1.1 | 10.4 ± 2.2 | 16.1 ± 1.7 | n.d. | 17.2 ± 5.7 | n.d. | n.d. |
| ThT-HE | PBS150K | 17.6 ± 3.6 | 10.6 ± 2.9 | 23.9 ± 1.4 | 40.0 ± 9.0 | n.d. | 20.9 ± 2.8 | n.d. | n.d. |
|  | PBS153NM | n.d. | n.d. | 13.7 ± 1.4 | 12.3 ± 1.8 | n.d. | 28.5 ± 9.7 | n.d. | n.d. | n.d.: Although an accurate value could not be measured, Kd was assumed to be > 40 nM

EXAMPLES

The present invention is described below by way of Examples. However, the present invention is not limited to the embodiments in the following Examples.

Example 1

1. Preparation of Circular DNA Template (1) A mixture was prepared with 20 μL of 5 μM single-stranded DNA (55mer) (final concentration, 0.5 μM), 20 μL of 10×attached buffer, 10 μL of 50 mM $MnCl_2$ (final concentration, 2.5 mM), 40 μL of 5 M betaine (final concentration, 1 M), 10 μL of 100 U/μL CircLigase (final concentration, 5 U/μL), and 100 μL of water (200 μL in total).

(2) The mixture was incubated at 60° C. for 16 hours.

(3) Generation of single-stranded circular DNA was confirmed by carrying out PAGE purification.

```
Single-stranded DNA (55mer):
phosphate-
                                      (SEQ ID NO: 9)
CCCCAAAAAGGAGCTTGAGGTTCTCCTTTAAAACCTTCCCCACCCTCCCC
ACCCT
```

Reagent Used:
CircLigase II ssDNA Ligase (Epicentre Technologies, WI, USA)

2. RCA (1) Preparation of Solution

Positive Control (POS_SYBR Gold and POS_ThT Derivative)

A mixture was prepared with 2 μL of 200 nM circular DNA template (final concentration, 20 nM), 2 μL of 1.6 μM DNA primer <1> (final concentration, 160 nM), 2 μL of 10×attached buffer, 2 μL of 10×attached BSA solution, 2 μL of 10 mM dNTPs (final concentration, 1 mM), 2 μL of 1 U/μL Phi29 Polymerase (final concentration, 0.1 U/μL), and 8 μL of water (20 μL in total).

Only Template and Primer (Sa1 to 6 and Ta1 to 6)

A mixture was prepared with 2 μL of 200 nM circular DNA (final concentration, 20 nM), 2 μL of 1.6 μM DNA primer (see Table 2) (final concentration, 160 nM), 2 μL of 10×attached buffer, 2 μL of 10×attached BSA solution, 2 μL of 10 mM dNTPs (final concentration, 1 mM), 2 μL of 1 U/μL Phi29 Polymerase (final concentration, 0.1 U/μL), and 8 μL of water (20 μL in total).

Template, Primer, and Target RNA (Sb1 to 6 and Tb1 to 6)

A mixture was prepared with 2 μL of 200 nM circular DNA (final concentration, 20 nM), 2 μL of 1.6 μM DNA primer (see Table 2) (final concentration, 160 nM), 2 μL of 800 nM target RNA (80 nM), 2 μL of 10×attached buffer, 2 μL of 10×attached BSA solution, 2 μL of 10 mM dNTPs (final concentration, 1 mM), 2 μL of 1 U/μL Phi29 Polymerase (final concentration, 0.1 U/μL), and 6 μL of water (20 μL in total).

TABLE 2

Figures 3, 4:
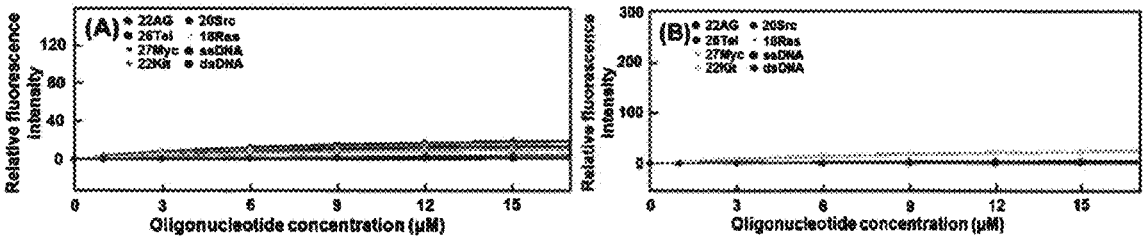
Figures 3, 4, 5:
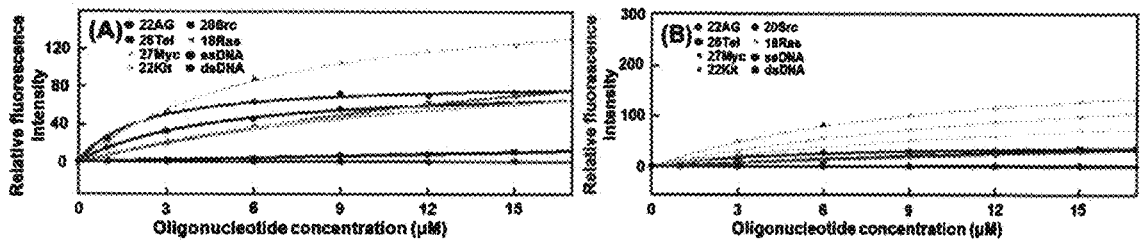

Correspondence table for primers (corresponding to FIG. 5)

|    | 1     | 2           | 3           | 4           | 5           | 6           |
|----|-------|-------------|-------------|-------------|-------------|-------------|
| Sa | water | DNA primer ② | DNA primer ③ | DNA primer ④ | DNA primer ⑤ | DNA primer ⑥ |
| Sb | water | DNA primer ② | DNA primer ③ | DNA primer ④ | DNA primer ⑤ | DNA primer ⑥ |
| Ta | water | DNA primer ② | DNA primer ③ | DNA primer ④ | DNA primer ⑤ | DNA primer ⑥ |
| Tb | water | DNA primer ② | DNA primer ③ | DNA primer ④ | DNA primer ⑤ | DNA primer ⑥ |

The positional relationships among the primers, the target RNA, and the circular DNA are shown in FIG. 4.

DNA primer <1> (20mer)
(SEQ ID NO: 10)
GGA AGG TTT TAA AGG AGA AC

DNA primer <2> (16mer)
(SEQ ID NO: 11)
GGA TCA GGC CAT TTT T

DNA primer <3> (18mer)
(SEQ ID NO: 12)
GGA TCA GGC CAT TTT TGG

DNA primer <4> (19mer)
(SEQ ID NO: 13)
GGA TCA GGC CAT TTT TGG G

DNA primer <5> (20mer)
(SEQ ID NO: 14)
GGA TCA GGC CAT TTT TGG GG

DNA primer <6> (21mer)
(SEQ ID NO: 15)
GGA TCA GGC CAT TTT TGG GGA

Target RNA (40mer)
(SEQ ID NO: 16)
GGG UUG CCC AAA GGA GAA CCU CAA GCU CCU GGC CUG AUC C Reagent Used:
phi29 DNA Polymerase (New England Biolabs Japan, Tokyo, Japan)

(2) Polymerase Reaction

The solution prepared in (1) was incubated at 37° C. for 2 hours.

(3) Visual Detection

To 16 μL of the reaction solution of (2), 4 μL of 5×PBS153NM buffer was added. The resulting mixture was subjected to annealing by decreasing the temperature from 94° C. to 25° C. at a step of 0.5° C.

A mixture was prepared with 10 μL of the solution after the annealing and 2 μL of a fluorescent dye (for Sa and Sb, SYBR Gold solution 800-fold diluted with 1×PBS153NM buffer, 4800-fold final concentration; or for Ta and Tb, 30 μM ThT derivative solution prepared by dissolution in 1×phosphate buffer, 5-μM final concentration), and the mixture was incubated at 25° C. for 30 minutes. The prepared solutions were irradiated with UV using a 256-nm UV lamp, and a photograph was taken with a camera equipped with a cut-off filter (which cuts off wavelengths shorter than 460 nm).

Reagents Used:
ThT (thioflavin T) derivative (ThT-HE)
SYBR Gold Life Technologies Japan Ltd., Tokyo, Japan
5×PBS153NM
50 mM $HPO_4^{2-}$, 730 mM $Cl^-$, 765 mM Nat, 13.5 mM $K^+$, 12.5 mM $Mg^{2+}$ pH 7.4
1×PBS153NM
10 mM $HPO_4^{2-}$, 146 mM $Cl^-$, 153 mM Nat, 2.7 mM $K^+$, 2.5 mM $Mg^{2+}$ pH 7.4

The fluorescence intensity of SYBR Gold changes depending on the nucleic acid concentration. On the other hand, the fluorescence intensity of a ThT derivative solution changes depending on the guanine quadruplex concentration. Accordingly, samples to which SYBR Gold was added show high background. On the other hand, ThT derivatives are expected to enable highly sensitive detection of the progress of the reaction independently of the nucleic acid concentration.

The polymerase reaction preferably proceeds in the presence of the RNA which is the target from the viewpoint of the design. Therefore, Sa and Ta are expected to show no emission of fluorescence.

The length of the primer is preferably one which does not allow the reaction to proceed in the presence of only the template and the primer. The present study was carried out for lengths of 16, 18, 19, 20, and 21mers The results are shown in FIG. 5.

First, in terms of POS_SYBR and the POS_ThT derivative, it can be seen that both of these showed emission of fluorescence due to progress of the reaction.

Fluorescence could be detected from neither Sa1 nor Ta1, which are negative controls (containing neither primer nor RNA).

The reaction did not proceed with Sb1 and Tb1 since they are mixed solutions in which the template and the RNA are contained, but no primer is contained. However, Sb1 showed emission of fluorescence by SYBR Gold due to the presence of an RNA concentration. On the other hand, in the case of Tb1, the reaction does not proceed, and therefore no guanine quadruplex is generated. Thus, no fluorescence was found.

In the cases of Sa2 to Sa6 and Ta2 to Ta6, the reaction is originally expected not to proceed since the RNA is absent. However, it is thought that the reaction proceeded in the cases of Ta5 and 6 due to hybridization of the DNA primer alone with the template. In terms of the fluorescence, Sa2 to Sa6 showed rather higher background of the fluorescence intensity due to the presence of the primers. On the other hand, Ta2 to Ta4, with which no reaction occurred, hardly showed fluorescence.

Based on comparison of the change in the reaction caused by addition of the single-stranded RNA, Ta2 did not cause the reaction to proceed, while Tb3 and 4 were found to have caused the reaction to proceed. On the other hand, comparison of Sa3 and 4 with Sb3 and 4 did not allow the judgment because of the high background.

Thus, detection of the presence or absence of the RNA with SYBR Gold was impossible because it stains nucleic acid itself, and hence its addition causes emission of fluorescence even in the absence of the RNA.

On the other hand, detection of the presence or absence of the RNA with the ThT derivative was found to be possible because it stains guanine quadruplex, and hence it does not cause emission of fluorescence in the absence of the RNA, while it causes emission of fluorescence in the presence of the RNA. It was also found, however, that amplification reaction occurs even in the absence of the RNA in cases where the primer portion which hybridizes with the single-stranded circular DNA is too long, and that the length of the primer portion which hybridizes with the single-stranded circular DNA is therefore preferably 7 to 8 bases.

Example 2

Figures 3, 4, 5, 6:
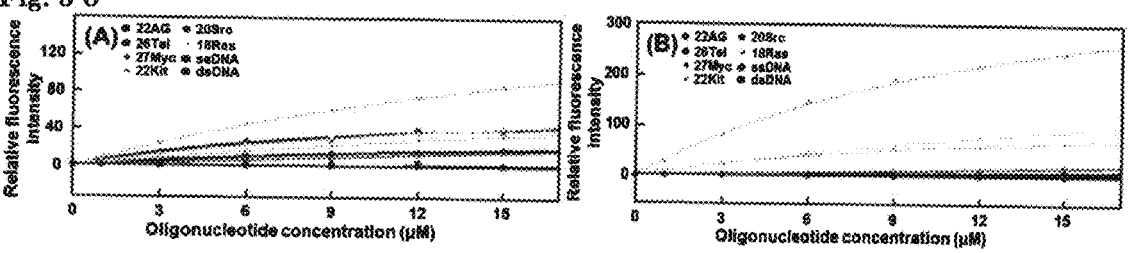
Figure 4:
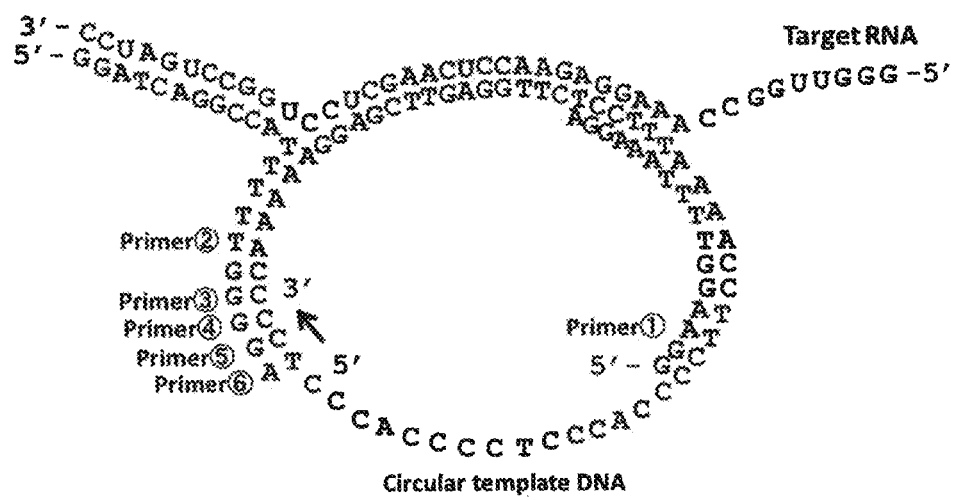
Figure 5:
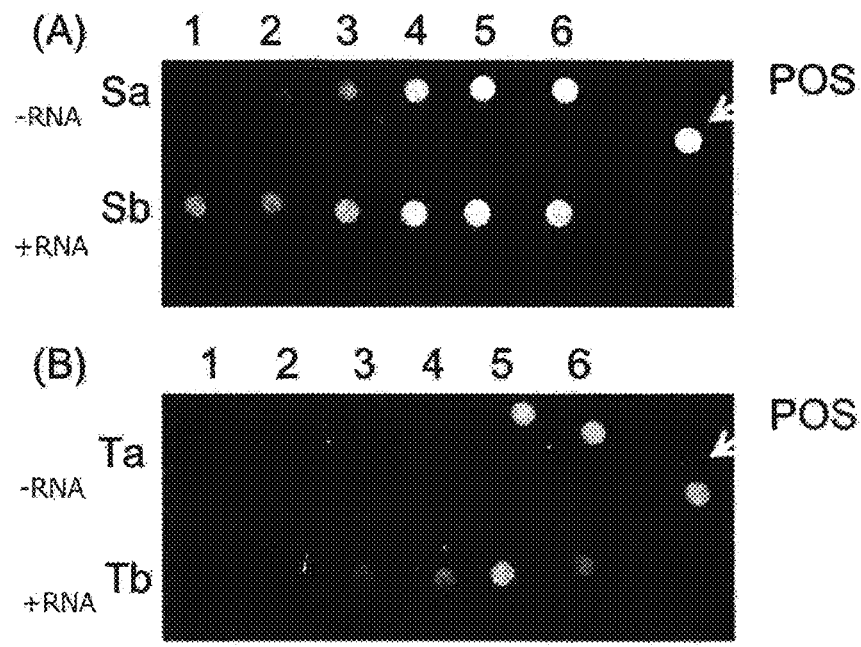
Figure 6:
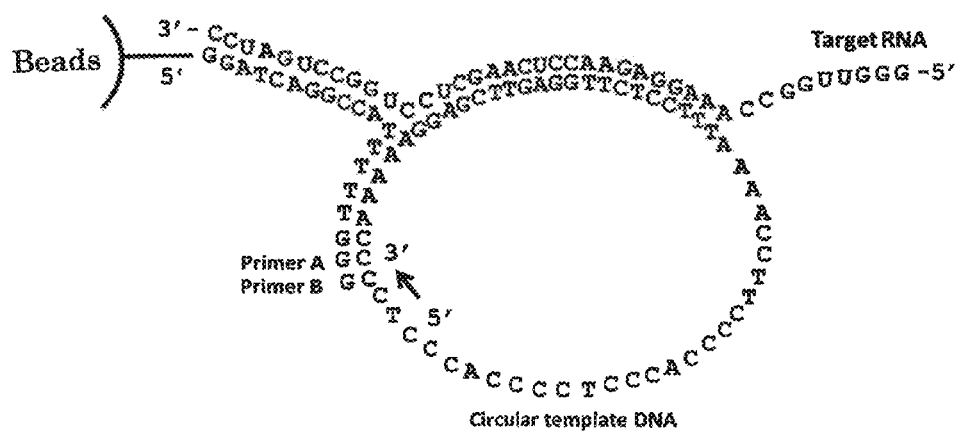

Detection Method 2 (RCA Using Streptavidin Beads) (FIG. 6)

[1] Preparation of Circular DNA Template (1) A mixture was prepared with 20 μL of 5 μM single-stranded DNA (55mer) (final concentration, 0.5 μM), 20 μL of 10×attached buffer, 10 μL of 50 mM $MnCl_2$ (final concentration, 2.5 mM), 40 μL of 5 M betaine (final concentration, 1 M), 10 μL of 100 U/μL CircLigase (final concentration, 5 U/μL), and 100 μL of water (200 μL in total).

(2) The mixture was incubated at 60° C. for 16 hours.

(3) PAGE purification was carried out.

```
Single-stranded DNA (55mer):
phosphate-
                                       (SEQ ID NO: 17)
CCCCAAAAAGGAGCTTGAGGTTCTCCTTTAAAACCTTCCCCACCCTCCCC
ACCCT
```

Reagent Used:
CircLigase II ssDNA Ligase (Epicentre Technologies, WI, USA)

[2] Preparation of Primer-bound Streptavidin Beads (1) To streptavidin-bearing magnetic beads (which are theoretically capable of binding to 4.5 pmol of biotin), 50 μL of 1×Phi29 polymerase buffer was added. By drawing the beads with a magnet, the 1×Phi29 polymerase buffer was removed. This was carried out twice.

(2) To (1), 1 μL of 1.6 μM 5'-biotinylated DNA primer A or B (prepared in 1×Phi29 polymerase buffer) was added, and the resulting mixture was incubated at 37° C. for 30 minutes.

(3) 50 μL of 1×Phi29 polymerase buffer was added to (2). By drawing the beads with a magnet, the 1×Phi29 polymerase buffer was removed. This was carried out twice.

Oligomers Used:

```
5'-biotinylated DNA primer A (18mer)
                               (SEQ ID NO: 18)
5'-biotin-GGA TCA GGC CAT TTT TGG-3'

5'-biotinylated DNA primer B (19mer)
                               (SEQ ID NO: 19)
5'-biotin-GGA TCA GGC CAT TTT TGG G-3'
```

Reagent Used:
Streptavidin Mag Sepharose (GE Healthcare Japan, Tokyo, Japan)

[3] Preparation of Samples (1) Reaction

Use of 5'-biotinylated DNA primer A=Sample <2>
Use of 5'-biotinylated DNA primer B=Sample <4>

With the prepared primer-bound streptavidin beads, 1 μL of 200 nM circular DNA template (final concentration, 20 nM), 1 μL of target RNA (final concentration, 80 nM), 1 μL of 10×attached buffer, 1 μL of 10×attached BSA solution, 1 μL of 10 mM dNTPs (final concentration, 1 mM), 1 μL of 1 U/μL Phi29 Polymerase (final concentration, 0.1 U/μL), and 4 μL of water were mixed (10 μL in total).

(1) Negative control (no target RNA)

Use of 5'-biotinylated DNA primer A=Sample <1>
Use of 5'-biotinylated DNA primer B=Sample <3>

With the prepared primer-bound streptavidin beads, 1 μL of 200 nM circular DNA template (final concentration, 20 nM), 1 μL of 10×attached buffer, 1 μL of 10×attached BSA solution, 1 μL of 10 mM dNTPs (final concentration, 1 mM), 1 μL of 1 U/μL Phi29 Polymerase (final concentration, 0.1 U/μL), and 5 μL of water were mixed (10 μL in total).

(2) Reagent and the Like Used:

phi29 DNA Polymerase (New England Biolabs Japan, Tokyo, Japan)

1×PBS153NM: 10 mM $HPO_4^{2-}$, 146 mM Cr, 153 mM Nat, 2.7 mM K$^+$, 2.5 mM Mg$^{2+}$ pH 7.4

[4] Polymerase Reaction

The solution prepared in [3] was incubated at 37° C. for 2 hours.

[5] Addition of Dye Liquid (1) 50 μL of 1×PBS153NM buffer was added. By drawing the beads with a magnet, the 1×PBS153NM buffer was removed. This was carried out twice.

(2) 30 μL of a ThT-HE solution (ThT-HE: 15 μM; PBS153NM Buffer: 1×) was added to (1) to prepare a reaction liquid. The final concentration of ThT-HE was 5 μM, and the concentration of PBS153NM Buffer was 1×.

[6] Visual Detection

After the addition of the dye liquid, the reaction liquid was irradiated with UV using a 410-nm UV lamp, and a photograph was taken with a camera equipped with a cut-off filter (which cuts off wavelengths shorter than 460 nm).

[7] Results

Figure 7:
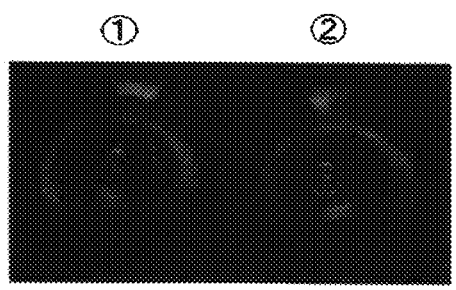
FIG. 7 shows diagrams (photographs) showing the result of the experiment in Example 2.
Figure 7:
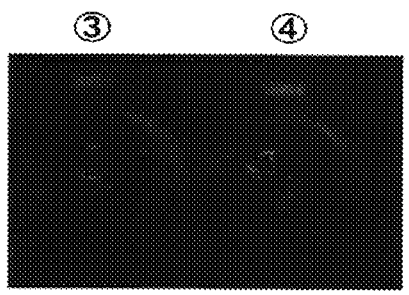

As a result of the reaction using the primer-bound beads, better visibility of fluorescence could be achieved by use of any of the primers, relative to a method using no beads (Method 1) (FIG. 7).

Example 3

Detection Method 3 (RCA Using Two Kinds of Templates)

[1] Preparation of Templates (1) A mixture was prepared with 20 μL of 5 μM single-stranded DNA (Cid_Pre_T: 67mer; Cid_Mai_T: 62mer) (final concentration, 0.5 μM), 20 μL of 10×attached buffer, 10 μL of 50 mM MnCl2 (final concentration, 2.5 mM), 40 μL of 5 M betaine (final concentration, 1 M), 10 μL of 100 U/μL CircLigase (final concentration, 5 U/μL), and 100 μL of water (200 μL in total).

(2) The mixture was incubated at 60° C. for 24 hours.

(3) PAGE purification was carried out.

Oligomers Used:

```
Cid_Pre_T (67mer)
Phosphate-
                                       (SEQ ID NO: 20)
CCCCAAAAAGGAGCTTGAGGTTCTCCTTTAAAAAGAAGCTGTTGTATTGT
TGTCGAAGAAGAAAGT Cid_Mai_T (62mer)
Phosphate-
                                       (SEQ ID NO: 21)
CCCAACCCTACCCACCCTCAAGAAAAAAAAGTGATAATTGTTGTCGAAGA
AGAAAAAAATT
```

Reagent Used:

CircLigase II ssDNA Ligase (Epicentre Technologies, WI, USA)

[2] Sequences of Oligonucleic Acids (DNAs)

```
Circular Cid_Pre_T: (67mer)
                                       (SEQ ID NO: 20)
CCC CAA AAA GGA GCT TGA GGT TCT CCT TTA AAA AGA
AGC TGT TGT ATT GTT GTC GAA GAA GAA AGT
```

Both ends were bound for circularization.

```
Circular Cid_Mai_T: (62mer)
                                       (SEQ ID NO: 21)
CCC AAC CCT ACC CAC CCT CAA GAA AAA AAA GTG ATA
ATT GTT GTC GAA GAA GAA AAA AAT T
```

Both ends were bound for circularization.

```
Cid_Pre_PP: (20mer)
                                       (SEQ ID NO: 22)
AAC CTC AAG CTC CTT TTT GG Cid_P18: (18mer)
                                       (SEQ ID NO: 23)
GGA TCA GGC CAT TTT TGG Cid_Mai_PP: (22mer)
                                       (SEQ ID NO: 24)
TCT TCG ACA ACA ATT ATC ACT T Cid_Mai_P18: (18mer)
                                       (SEQ ID NO: 25)
GAA GCT GTT GTT ATC ACT
```

[3] Final Concentrations of Reagents

Pre-amplifier template (circular Cid_Pre_T) 4 nM
Pre-amplifier primer (Cid_P18 or Cid_Pre_PP) 40 nM
Target RNA 2 nM
Pre-amplifier template (circular Cid_Mai_T) 40 nM
Main-amplifier primer (Cid_Mai_P18 or Cid_Mai_PP) 200 nM
Phi29 polymerase buffer 1×
BSA (Bovine serum albumin) 0.1 mg/μL
dNTPs (dATP, TTP, dGTP, dCTP) 1 mM
Phi29 polymerase 0.05 U/μL

[4] Preparation of Samples

<1> Negative Control

To 5 μL of water, 1 μL each of 10×Phi29 polymerase buffer (final concentration, 1×), 1 mg/1 μL BSA solution (final concentration, 0.1 mg/μL), 10 mM dNTPs (final concentration, 1 mM), 400 nM Main-amplifier template (final concentration, 40 nM), and 0.5 U/μL Phi29 polymerase (final concentration, 0.05 U/μL) was added, and the resulting mixture was mixed well (final volume, 10 μL).

<2> Negative Control (Confirmation of Occurrence of No Reaction with Cid_Mai_P18 Alone)

To 4 μL of water, 1 μL each of 10×Phi29 polymerase buffer (final concentration, 1×), 1 mg/1 μL BSA solution (final concentration, 0.1 mg/μL), 10 mM dNTPs (final concentration, 1 mM), 400 nM Main-amplifier template (final concentration, 40 nM), 2 μM Cid_Mai_P18 (final concentration, 200 nM), and 0.5 U/μL Phi29 polymerase (final concentration, 0.05 U/μL) was added, and the resulting mixture was mixed well (final volume, 10 μL).

<3> Negative Control (Confirmation of Occurrence of No Reaction by Addition of Cid_P18)

To 4 μL of water, 1 μL each of 10×Phi29 polymerase buffer (final concentration, 1×), 1 mg/1 μL BSA solution (final concentration, 0.1 mg/μL), 10 mM dNTPs (final concentration, 1 mM), 400 nM Main-amplifier template (final concentration, 40 nM), 400 nM Cid_P18 (final concentration, 40 nM), and 0.5 U/μL Phi29 polymerase (final concentration, 0.05 U/μL) was added, and the resulting mixture was mixed well (final volume, 10 μL).

<4> Negative Control (Confirmation of Occurrence of No Reaction by Addition of RNA)

To 4 μL of water, 1 μL each of 10×Phi29 polymerase buffer (final concentration, 1×), 1 mg/1 μL BSA solution (final concentration, 0.1 mg/μL), 10 mM dNTPs (final concentration, 1 mM), 400 nM Main-amplifier template (final concentration, 40 nM), 20 nM target RNA (final concentration, 2 nM), and 0.5 U/μL Phi29 polymerase (final concentration, 0.05 U/μL) was added, and the resulting mixture was mixed well (final volume, 10 μL).

<5> Negative Control (Confirmation of Occurrence of No Reaction in Main Side by Progress of Reaction in pre Side)

Figure 8:
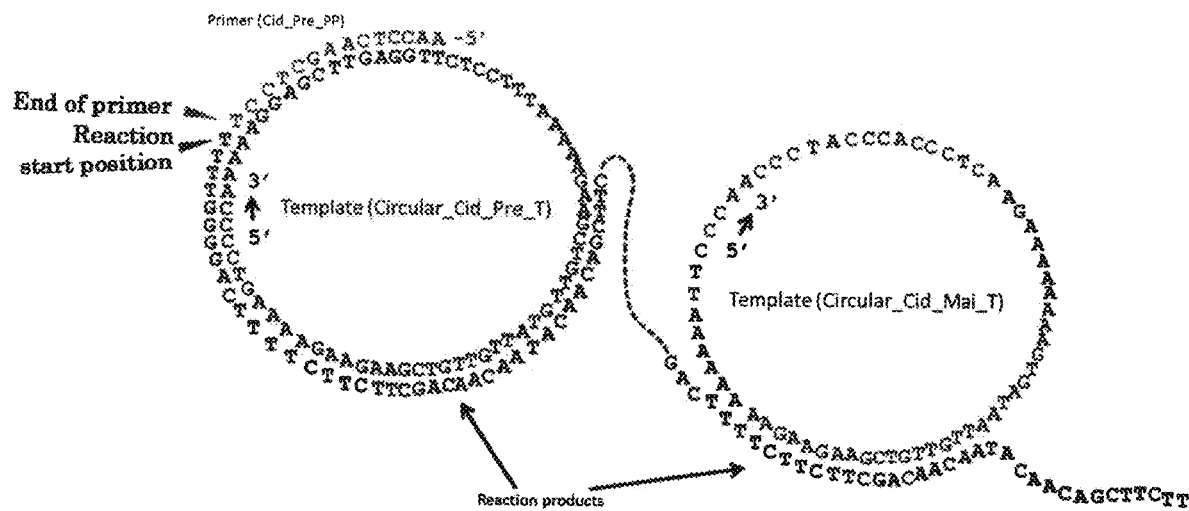
FIG. 8 shows a diagram showing the sequences of the single-stranded circular DNA template and the primer in Example 3 (Sample <5>).

To 3 μL of water, 1 μL each of 10×Phi29 polymerase buffer (final concentration, 1×), 1 mg/1 μL BSA solution (final concentration, 0.1 mg/μL), 10 mM dNTPs (final concentration, 1 mM), 40 nM Pre-amplifier template (final concentration, 4 nM), 400 nM Cid_Pre_PP (final concentration, 40 nM), 400 nM Main-amplifier template (final concentration, 40 nM), and 0.5 U/µL Phi29 polymerase (final concentration, 0.05 U/µL) was added, and the resulting mixture was mixed well (final volume, 10 µL). (FIG. 8)

<6> Negative Control (Confirmation of Occurrence of No Reaction in Main Side by Progress of Reaction in pre Side)

Figure 9:
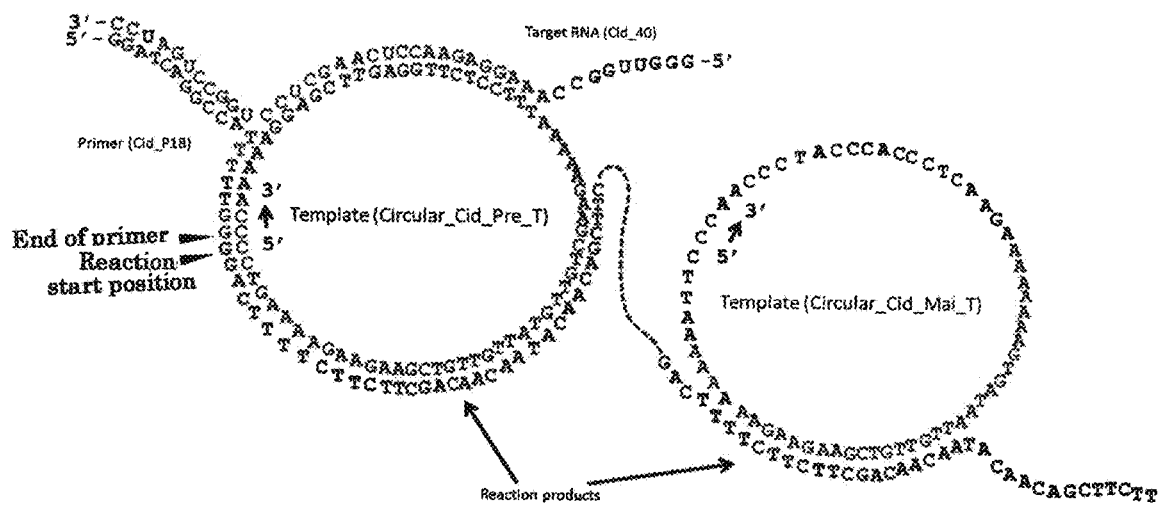
FIG. 9 shows a diagram showing the sequences of the target RNA, single-stranded circular DNA template, and primers in Example 3 (Sample <6>).

To 2 µL of water, 1 µL each of 10×Phi29 polymerase buffer (final concentration, 1×), 1 mg/1 µL BSA solution (final concentration, 0.1 mg/µL), 10 mM dNTPs (final concentration, 1 mM), 40 nM Pre-amplifier template (final concentration, 4 nM), 400 nM Cid_P18 (final concentration, 40 nM), 20 nM target RNA (final concentration, 2 nM), 400 nM Main-amplifier template (final concentration, 40 nM), and 0.5 U/µL Phi29 polymerase (final concentration, 0.05 U/µL) was added, and the resulting mixture was mixed well (final volume, 10 µL). (FIG. 9)

<7> Positive Control

Figure 10:
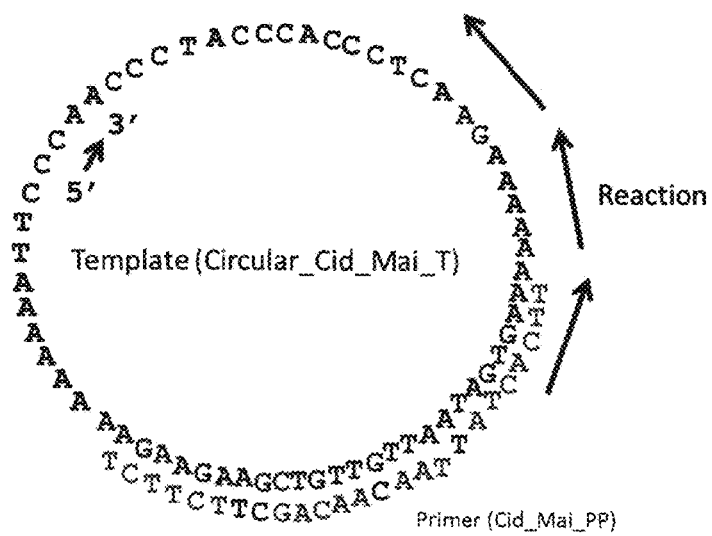
FIG. 10 shows a diagram showing the sequences of the single-stranded circular DNA template and the primers in Example 3 (Sample <7>).

To 4 µL of water, 1 µL each of 10×Phi29 polymerase buffer (final concentration, 1×), 1 mg/1 µL BSA solution (final concentration, 0.1 mg/µL), 10 mM dNTPs (final concentration, 1 mM), 400 nM Main-amplifier template (final concentration, 40 nM), 2 µM Cid_Mai_PP (final concentration, 200 nM), and 0.5 U/µL Phi29 polymerase (final concentration, 0.05 U/µL) was added, and the resulting mixture was mixed well (final volume, 10 µL). (FIG. 10)

<8> Positive Control (Confirmation of Occurrence of Reaction in Main Side by Progress of Reaction in pre Side)

Figure 11:
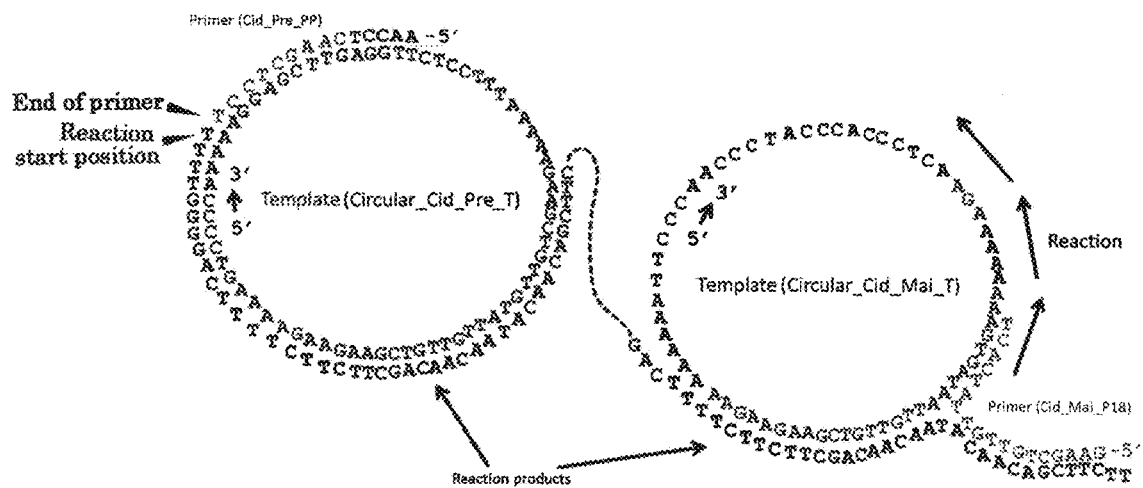
FIG. 11 shows a diagram showing the sequences of the single-stranded circular DNA template and the primers in Example 3 (Sample <8>).

To 2 µL of water, 1 µL each of 10×Phi29 polymerase buffer (final concentration, 1×), 1 mg/1 µL BSA solution (final concentration, 0.1 mg/µL), 10 mM dNTPs (final concentration, 1 mM), 40 nM Pre-amplifier template (final concentration, 4 nM), 400 nM Cid_Pre_PP (final concentration, 40 nM), 400 nM Main-amplifier template (final concentration, 40 nM), 2 µM Cid_Mai_P18 (final concentration, 200 nM), and 0.5 U/µL Phi29 polymerase (final concentration, 0.05 U/µL) was added, and the resulting mixture was mixed well (final volume, 10 µL). (FIG. 11)

<9> Reaction

Figure 12:
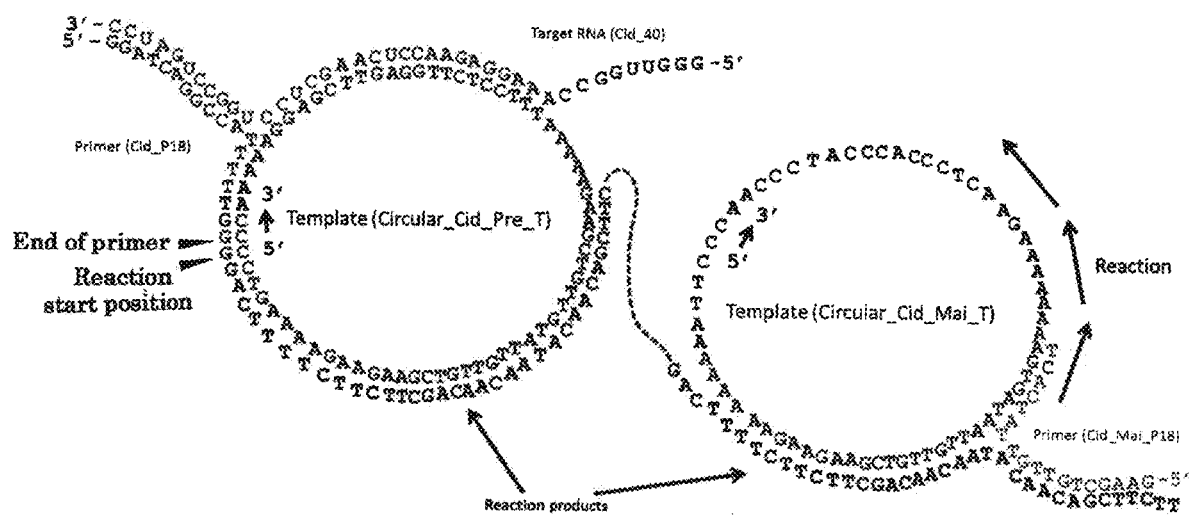
FIG. 12 shows a diagram showing the sequences of the target RNA, single-stranded circular DNA template, and primers in Example 3 (Sample <9>).

To 1 µL of water, 1 µL each of 10×Phi29 polymerase buffer (final concentration, 1×), 1 mg/1 µL BSA solution (final concentration, 0.1 mg/µL), 10 mM dNTPs (final concentration, 1 mM), 40 nM Pre-amplifier template (final concentration, 4 nM), 400 nM Cid_P18 (final concentration, 40 nM), 20 nM target RNA (final concentration, 2 nM), 400 nM Main-amplifier template (final concentration, 40 nM), 2 µM Cid_Mai_P18 (final concentration, 200 nM), and 0.5 U/µL Phi29 polymerase (final concentration, 0.05 U/µL) was added, and the resulting mixture was mixed well (final volume, 10 µL). (FIG. 12)

[5] Reaction

Preparation of the reaction liquid was carried out using a 96-well plate. The reaction was allowed to proceed at 37° C. for 1 hour.

[6] Addition of Dye Liquid

To the reaction liquid, 20 µL of a ThT-HE solution (ThT-HE: 15 µM; PBS153NM Buffer: 1.5×) was added. The final concentration of ThT-HE was 5 µM, and the concentration of PBS153NM Buffer was 1×.

1×PBS153NM 10 mM $HPO_4^{2-}$, 146 mM $Cl^-$, 153 mM Nat, 2.7 mM $K^+$, 2.5 mM $Mg^{2+}$ pH 7.4

[7] Visual Detection

After the addition of the dye liquid, the reaction liquid was irradiated with UV using a 410 nm UV lamp, and a photograph was taken with a camera equipped with a cut-off filter (which cuts off wavelengths shorter than 460 nm).

[8] Results

Figure 13:
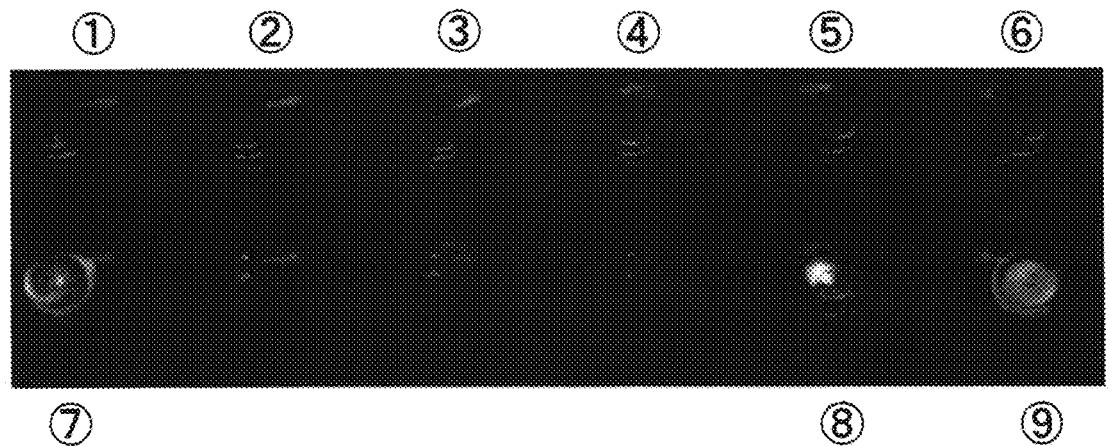
FIG. 13 shows a diagram (photograph) showing the result of the experiment in Example 3.

Generation of guanine quadruplex occurred in the reactions of <7>, <8>, and <9> (FIG. 13). The other reactions, which are negative controls, hardly showed fluorescence. This indicates high capacity to control the reaction in the Main side. Moreover, high detection ability could be achieved since the concentration of the target RNA could be decreased compared to the cases where only one circular template was used.

DESCRIPTION OF SYMBOLS

10 . . . Single-stranded circular DNA template; 11 . . . target RNA; 12 . . . oligonucleotide primer; 13 . . . amplification product; 101 . . . sequence complementary to the first portion; 102 . . . primer-binding sequence; 103 . . . sequence complementary to a guanine quadruplex-forming sequence; 104 . . . sequence containing a guanine quadruplex; 105 . . . guanine quadruplex detection reagent; 111 . . . first portion; 112 . . . second portion; 121 . . . sequence complementary to the second portion; 122 . . . sequence complementary to the primer-binding portion.

20 . . . Single-stranded circular DNA template; 21 . . . target RNA; 22 . . . first oligonucleotide primer; 23 . . . first amplification product; 24 . . . second single-stranded circular DNA template; 25 . . . second oligonucleotide primer; 26 . . . second amplification product; 201 . . . sequence complementary to the first portion; 202 . . . first primer-binding sequence; 203 . . . second single-stranded circular DNA-binding sequence; 204 . . . portion adjacent to the 5'-side of 203; 243 . . . sequence complementary to a guanine quadruplex-forming sequence; 261 . . . sequence containing a guanine quadruplex; 262 . . . guanine quadruplex detection reagent; 211 . . . first portion; 212 . . . second portion; 221 . . . sequence complementary to the second portion; 222 . . . sequence complementary to the first primer-binding portion; 231 . . . region complementary to 203; 232 . . . region complementary to the portion 204; 241 . . . same sequence as the second single-stranded circular DNA-binding sequence 203; 242 . . . second primer-binding sequence; 251 . . . same sequence as the portion 204; 252 . . . sequence complementary to the second primer-binding sequence 242 of the second single-stranded circular DNA.

What is claimed is:

1. A nucleic acid detection kit comprising:
   (i) a single-stranded circular DNA template containing:
       a sequence of 10 to 30 bases complementary to a first portion of a target nucleic acid; and
       a primer-binding sequence of 7 to 8 bases adjacent to 5'-side thereof; and
   (ii) an oligonucleotide primer containing:
       a sequence of 8 to 15 bases complementary to a second portion adjacent to the 3'-side of the first portion of the target nucleic acid; and
       a sequence of 7 to 8 bases adjacent to the 3'-side thereof and complementary to the primer-binding sequence of the single-stranded circular DNA template.

2. A nucleic acid detection kit comprising:
   (i) a first single-stranded circular DNA template containing:
       a sequence of 10 to 30 bases complementary to a first portion of a target nucleic acid;
       a first primer-binding sequence of 7 to 8 bases adjacent to the 5'-side thereof; and
       a second single-stranded circular DNA-binding sequence;
   (ii) a first oligonucleotide primer containing:
       a sequence of 8 to 15 bases complementary to a second portion adjacent to the 3'-side of the first portion of the target nucleic acid; and a sequence of 7 to 8 bases adjacent to the 3'-side thereof and complementary to the first primer-binding portion of the first single-stranded circular DNA template;

(iii) a second single-stranded circular DNA containing:

the same sequence as the second single-stranded circular DNA-binding sequence of the first single-stranded circular DNA; and a second primer-binding sequence adjacent to the 5'-side thereof; and (iv) a second oligonucleotide primer containing:

the same sequence as the portion adjacent to the 5'-side of the second single-stranded circular DNA-binding sequence of the first single-stranded circular DNA; and a sequence adjacent to 3'-side thereof and complementary to the second primer-binding sequence of the second single-stranded circular DNA.

3. A method for detecting a target nucleic acid using the kit according to claim 1, said method comprising the steps of:

hybridizing said single-stranded circular DNA template and said primer with the target nucleic acid;

performing nucleic acid amplification reaction based on the target nucleic acid by rolling circle amplification; and detecting a product of the nucleic acid amplification reaction.

4. The nucleic acid detection kit according to claim 1, wherein said kit further comprises (iii) a detection reagent and wherein said single-stranded circular DNA template further contains a sequence complementary to a detection reagent-binding sequence.

5. The nucleic acid detection kit according to claim 4, wherein said detection reagent-binding sequence is a guanine quadruplex-forming sequence, and said detection reagent is a guanine quadruplex-binding reagent.

6. The nucleic acid detection kit according to claim 5, wherein the sequence complementary to the guanine quadruplex-forming sequence comprises a $C_3N_{1-10}C_3N_{1-10}C_3N_{1-10}C_3$ sequence.

7. The nucleic acid detection kit according to claim 5, wherein said guanine quadruplex-binding reagent comprises a compound represented by the following General Formula (I):

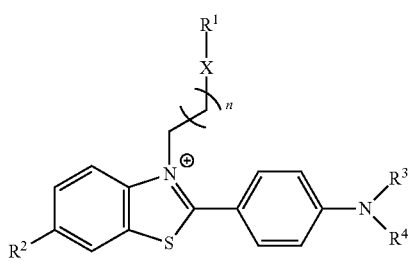

wherein $R^1$ represents hydrogen, or a hydrocarbon group which optionally contains one or more selected from the group consisting of O, S, and N;

$R^2$, $R^3$, and $R^4$ each independently represent a $C_1$-$C_5$ hydrocarbon group;

n represents an integer of 0 to 5; and

X represents O, S, or NH.

8. The nucleic acid detection kit according to claim 7, wherein the compound represented by General Formula (I) is represented by the following Formula (II) or (III):

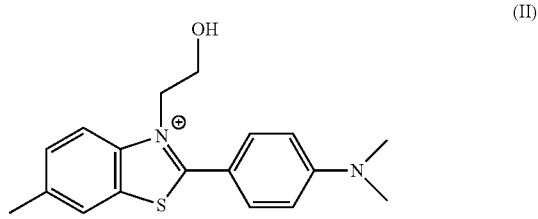

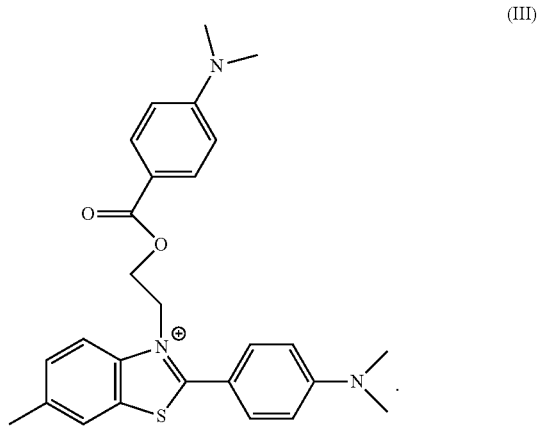

9. The method according to claim 3, wherein said target nucleic acid is RNA.

10. The nucleic acid detection kit according to claim 1, wherein said target nucleic acid is RNA.

11. The nucleic acid detection kit according to claim 2, wherein said target nucleic acid is RNA.

12. The nucleic acid detection kit according to claim 2, wherein said kit further comprises (v) a detection reagent and wherein said second single-stranded circular DNA further contains a sequence complementary to a detection reagent-binding sequence.

13. The nucleic acid detection kit according to claim 12, wherein said detection reagent-binding sequence is a guanine quadruplex-forming sequence, and said detection reagent is a guanine quadruplex-binding reagent.

14. The nucleic acid detection kit according to claim 13, wherein the sequence complementary to the guanine quadruplex-forming sequence comprises a $C_3N_{1-10}C_3N_{1-10}C_3N_{1-10}C_3$ sequence.

15. The nucleic acid detection kit according to claim 13, wherein said guanine quadruplex-binding reagent comprises a compound represented by the following General Formula (I):

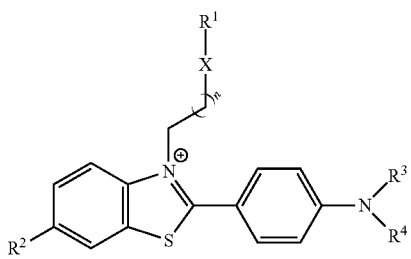

(I)

wherein $R^1$ represents hydrogen, or a hydrocarbon group which optionally contains one or more selected from the group consisting of O, S, and N;
$R^2$, $R^3$, and $R^4$ each independently represent a $C_1$-$C_5$ hydrocarbon group;
n represents an integer of 0 to 5; and
X represents O, S, or NH.

16. The nucleic acid detection kit according to claim 15, wherein the compound represented by General Formula (I) is represented by the following Formula (II) or (III):

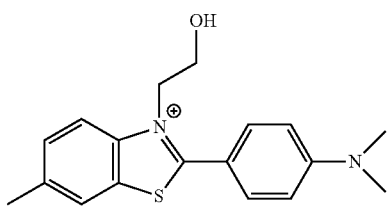

(II)

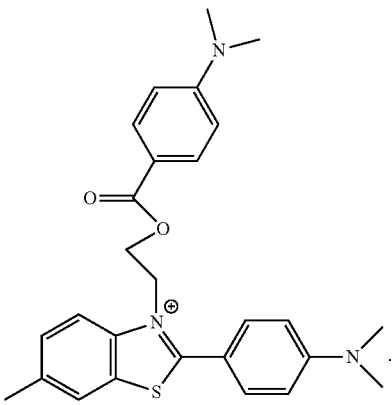

(III)

17. A method for detecting a target nucleic acid using the kit according to claim 2, said method comprising the steps of:

hybridizing said single-stranded circular DNA template and said primer with the target nucleic acid;

performing nucleic acid amplification reaction based on the target nucleic acid by rolling circle amplification; and detecting a product of the nucleic acid amplification reaction.

18. The method according to claim 17, wherein said target nucleic acid is RNA.

* * * * *

SEQUENCE LISTING

<160> NUMBER OF SEQ ID NOS: 25

<210> SEQ ID NO 1
<211> LENGTH: 22
<212> TYPE: DNA
<213> ORGANISM: Artificial Sequence
<220> FEATURE:
<223> OTHER INFORMATION: oligonucleotide

<400> SEQUENCE: 1

```
agggttaggg ttagggttag gg                                            22

<210> SEQ ID NO 2
<211> LENGTH: 22
<212> TYPE: DNA
<213> ORGANISM: Artificial Sequence
<220> FEATURE:
<223> OTHER INFORMATION: oligonucleotide

<400> SEQUENCE: 2
agggagggcg ctgggaggag gg                                            22

<210> SEQ ID NO 3
<211> LENGTH: 26
<212> TYPE: DNA
<213> ORGANISM: Artificial Sequence
<220> FEATURE:
<223> OTHER INFORMATION: oligonucleotide

<400> SEQUENCE: 3
ttagggttag ggttagggtt agggtt                                        26

<210> SEQ ID NO 4
<211> LENGTH: 27
<212> TYPE: DNA
<213> ORGANISM: Artificial Sequence
<220> FEATURE:
<223> OTHER INFORMATION: oligonucleotide

<400> SEQUENCE: 4
tggggagggt ggggagggtg gggaagg                                       27

<210> SEQ ID NO 5
<211> LENGTH: 20
<212> TYPE: DNA
<213> ORGANISM: Artificial Sequence
<220> FEATURE:
<223> OTHER INFORMATION: oligonucleotide

<400> SEQUENCE: 5
gggcggcggg ctgggcgggg                                               20

<210> SEQ ID NO 6
<211> LENGTH: 18
<212> TYPE: RNA
<213> ORGANISM: Artificial Sequence
<220> FEATURE:
<223> OTHER INFORMATION: oligonucleotide

<400> SEQUENCE: 6
gggaggggcg ggucuggg                                                 18

<210> SEQ ID NO 7
<211> LENGTH: 17
<212> TYPE: DNA
<213> ORGANISM: Artificial Sequence
<220> FEATURE:
<223> OTHER INFORMATION: oligonucleotide

<400> SEQUENCE: 7
gggttactac gaactgg                                                  17

<210> SEQ ID NO 8
<211> LENGTH: 17
<212> TYPE: DNA
```

```
<213> ORGANISM: Artificial Sequence
<220> FEATURE:
<223> OTHER INFORMATION: oligonucleotide

<400> SEQUENCE: 8
ccagttcgta gtaaccc                                                  17

<210> SEQ ID NO 9
<211> LENGTH: 55
<212> TYPE: DNA
<213> ORGANISM: Artificial Sequence
<220> FEATURE:
<223> OTHER INFORMATION: template DNA

<400> SEQUENCE: 9
ccccaaaaag gagcttgagg ttctccttta aaaccttccc caccctcccc accct        55

<210> SEQ ID NO 10
<211> LENGTH: 20
<212> TYPE: DNA
<213> ORGANISM: Artificial Sequence
<220> FEATURE:
<223> OTHER INFORMATION: primer 1

<400> SEQUENCE: 10
ggaaggtttt aaaggagaac                                               20

<210> SEQ ID NO 11
<211> LENGTH: 16
<212> TYPE: DNA
<213> ORGANISM: Artificial Sequence
<220> FEATURE:
<223> OTHER INFORMATION: primer 2

<400> SEQUENCE: 11
ggatcaggcc attttt                                                   16

<210> SEQ ID NO 12
<211> LENGTH: 18
<212> TYPE: DNA
<213> ORGANISM: Artificial Sequence
<220> FEATURE:
<223> OTHER INFORMATION: primer 3

<400> SEQUENCE: 12
ggatcaggcc atttttgg                                                 18

<210> SEQ ID NO 13
<211> LENGTH: 19
<212> TYPE: DNA
<213> ORGANISM: Artificial Sequence
<220> FEATURE:
<223> OTHER INFORMATION: primer 4

<400> SEQUENCE: 13
ggatcaggcc atttttggg                                                19

<210> SEQ ID NO 14
<211> LENGTH: 20
<212> TYPE: DNA
<213> ORGANISM: Artificial Sequence
<220> FEATURE:
<223> OTHER INFORMATION: primer 5

<400> SEQUENCE: 14
ggatcaggcc atttttgggg                                               20
```

<210> SEQ ID NO 15
<211> LENGTH: 21
<212> TYPE: DNA
<213> ORGANISM: Artificial Sequence
<220> FEATURE:
<223> OTHER INFORMATION: primer 6

<400> SEQUENCE: 15
ggatcaggcc atttttgggg a                                              21

<210> SEQ ID NO 16
<211> LENGTH: 40
<212> TYPE: RNA
<213> ORGANISM: Artificial Sequence
<220> FEATURE:
<223> OTHER INFORMATION: target RNA

<400> SEQUENCE: 16
ggguuggcca aaggagaacc ucaagcuccu ggccugaucc                          40

<210> SEQ ID NO 17
<211> LENGTH: 55
<212> TYPE: DNA
<213> ORGANISM: Artificial Sequence
<220> FEATURE:
<223> OTHER INFORMATION: template DNA

<400> SEQUENCE: 17
ccccaaaaag gagcttgagg ttctccttta aaaccttccc caccctcccc accct         55

<210> SEQ ID NO 18
<211> LENGTH: 18
<212> TYPE: DNA
<213> ORGANISM: Artificial Sequence
<220> FEATURE:
<223> OTHER INFORMATION: primer

<400> SEQUENCE: 18
ggatcaggcc attttttgg                                                 18

<210> SEQ ID NO 19
<211> LENGTH: 19
<212> TYPE: DNA
<213> ORGANISM: Artificial Sequence
<220> FEATURE:
<223> OTHER INFORMATION: primer

<400> SEQUENCE: 19
ggatcaggcc atttttggg                                                 19

<210> SEQ ID NO 20
<211> LENGTH: 67
<212> TYPE: DNA
<213> ORGANISM: Artificial Sequence
<220> FEATURE:
<223> OTHER INFORMATION: template DNA

<400> SEQUENCE: 20
ccccaaaaag gagcttgagg ttctccttta aaagaagct gttgtattgt tgtcgaagaa     60
gaaaagt                                                              67

<210> SEQ ID NO 21
<211> LENGTH: 62
<212> TYPE: DNA

<213> ORGANISM: Artificial Sequence
<220> FEATURE:
<223> OTHER INFORMATION: template DNA

<400> SEQUENCE: 21 cccaaccctca cccaccctca agaaaaaaaa gtgataattg ttgtcgaaga agaaaaaaaa    60
tt    62

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
aacctcaagc tcctttttgg    20

<210> SEQ ID NO 23
<211> LENGTH: 18
<212> TYPE: DNA
<213> ORGANISM: Artificial Sequence
<220> FEATURE:
<223> OTHER INFORMATION: primer

<400> SEQUENCE: 23
ggatcaggcc atttttgg    18

<210> SEQ ID NO 24
<211> LENGTH: 22
<212> TYPE: DNA
<213> ORGANISM: Artificial Sequence
<220> FEATURE:
<223> OTHER INFORMATION: primer

<400> SEQUENCE: 24
tcttcgacaa caattatcac tt    22

<210> SEQ ID NO 25
<211> LENGTH: 18
<212> TYPE: DNA
<213> ORGANISM: Artificial Sequence
<220> FEATURE:
<223> OTHER INFORMATION: primer

<400> SEQUENCE: 25
gaagctgttg ttatcact    18